(12) United States Patent
Rand

(10) Patent No.: US 8,455,197 B2
(45) Date of Patent: Jun. 4, 2013

(54) NUCLEIC ACID AMPLIFICATION

(75) Inventor: Keith Norman Rand, Frenchs Forest (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 96 days.

(21) Appl. No.: 12/681,603

(22) PCT Filed: Oct. 3, 2008

(86) PCT No.: PCT/AU2008/001475
§ 371 (c)(1), (2), (4) Date: Oct. 19, 2010

(87) PCT Pub. No.: WO2009/043112
PCT Pub. Date: Apr. 9, 2009

(65) Prior Publication Data
US 2011/0033851 A1 Feb. 10, 2011

(30) Foreign Application Priority Data
Oct. 4, 2007 (AU) .................................. 2007905445

(51) Int. Cl.
*C12Q 1/68* (2006.01)
*C12P 19/34* (2006.01)

(52) U.S. Cl.
USPC ............................ 435/6.12; 435/6.1; 435/6.11

(58) Field of Classification Search
None
See application file for complete search history.

(56) References Cited

U.S. PATENT DOCUMENTS

| 2005/0153333 A1 | 7/2005 | Sooknanan |
| 2005/0255486 A1 * | 11/2005 | Behlke et al. ........................ 435/6 |
| 2006/0014183 A1 | 1/2006 | Pfundheller |

FOREIGN PATENT DOCUMENTS

| WO | WO 03/074724 A2 | 9/2003 |
| WO | WO 2007/109850 A1 | 10/2007 |
| WO | WO 2008/064687 A1 | 6/2008 |

OTHER PUBLICATIONS

Reyes et al., "Linked Linear Amplification: A New Method for the Amplification of DNA," *Clinical chemistry*, 47:1, 31-40 (2001).
International Search Report mailed on Dec. 1, 2008, for International Application No. PCT/AU2008/001475 filed on Oct. 3, 2008, 3 pages.
Puskás, L.G. et al., "Reduction of Mispriming in Amplification Reactions with Restricted PCR," *Genome Research*, 1995, vol. 5, pp. 309-311.

* cited by examiner

*Primary Examiner* — Young J Kim
(74) *Attorney, Agent, or Firm* — Kilpatrick Townsend & Stockton LLP

(57) ABSTRACT

Provided herein is a method for the selective amplification of a target nucleotide sequence located within a nucleic acid molecule, the method comprising contacting the nucleic acid molecule ("template" molecule) with (i) at least one facilitator oligonucleotide, wherein the facilitator oligonucleotide includes at least one modification at or near its 3' terminus such that 3' extension from the facilitator oligonucleotide is blocked, and (ii) two or more oligonucleotide primers, at least one of which is an initiator primer modified such that the presence of the modification prematurely terminates complementary strand synthesis, wherein the facilitator oligonucleotide and the initiator primer bind to substantially the same or adjacent regions of the template nucleic acid molecule and the facilitator oligonucleotide further comprises sequences complementary to the target sequence 3' to the binding location of the initiator primer; and carrying out thermocyclic, enzymatic amplification such that the specific target sequence is selectively amplified.

24 Claims, 13 Drawing Sheets

```
Target DNA 5' GGCGTCGTGGGCGGTGTGGGATGCCGTTAAGTGTTCGGTGCTGGCTCACGCCTGTAATCCCAGCACTTTGGGAGGCCGAGGC 3'   AluRev <<TCGTGAAACCCTCCGGCTCCG 5' (SEQ ID NO:1)
           3' CCGCAGCACCCGCCACACCCTACCGCCAAATCACAAGCCACCGAGTGCGGACATTAGGGTCGTGAAACCCTCCGGCTCCG 5'                                 (SEQ ID NO:2)
                                                                                                                               (SEQ ID NO:28)

Initiator primer
(InAluPr3) 5' GGCGTCGTGGGCGGTGTGGGATGGCGTTAAGTGTT >> (SEQ ID NO:3)

Facilitator oligonucleotide
(InAluFol15) 5' GICGTCITGIGCGITGTIGGATIGCITTTAGTGTTCGGTΔGCTCACGCCTGTAATCCCTAAG (SEQ ID NO:4)
```

Figure 2

MUTB 5' CGACGGTGGGTGGTTGCTGTGTCCTGTGTCTACAGAGAAATCTCGATCCCTCTTAGAAGAGGCTAAGCGGAGGTCAGG 3' (SEQ ID NO:5)
     3' GCTGCCACCCACCAACGACACAGGACACAGATGTCTCTTTAGAGCTAGGAGAATCTTCTCCGATTCGCCTCCAGTCC 5'

NORB 5' CGACGGTGGGTGGTTGCTGTGTCCTGTGTCTACAGTGAAATCTCGATCCCTCTTAGAAGAGGCTAAGCGGAGGTCAGG 3' (SEQ ID NO:6)
     3' GCTGCCACCCACCAACGACACAGGACACAGATGTCACTTTAGAGCTAGGAGAATCTTCTCCGATTCGCCTCCAGTCC 5'

Figure 4

```
BFol3  5' CTACGTTGTTTTTTCTGTGTCCTGTGTCCTGTGTCTACAGAGAAATCTCGATGGAGAA              CommR3G  << AATCTTCTCCGATTCGCCTCCAGTCC 5'  (SEQ ID NO:7)
BRF2   5' CGACGGTGGGTGGTTGCTGCTGTGACCTGTG >>  (SEQ ID NO:9)                                AATCTTCTCCGATTCGCCTCCAGTCC 5'  (SEQ ID NO:8)
MUTB   3' GCTGCCACCCACCAACGACACAGGACACAGATGTCTCTTTAGAGCTAGAGGAGAATCTTCTCCGATTCGCCTCCAGTCC 5'  (SEQ ID NO:5)

BFol3  5' CTACGTTGTTTTTTCTGTGTCCTGTGTCCTGTGTCTACAGAGAAATCTCGATGGAGAA              CommR3G  << AATCTTCTCCGATTCGCCTCCAGTCC 5'
BRF2   5' CGACGGTGGGTGGTTGCTGCTGTGACCTGTG >>
NORB   3' GCTGCCACCCACCAACGACACAGGACACAGATGTCACTTTAGAGCTAGGAGAATCTTCTCCGATTCGCCTCCAGTCC 5'  (SEQ ID NO:6)
```

Figure 5

M  5' ATTCCGCCCTGTGGGATTATTTTATAAGGTTAACAAAAAAACGTATCCGCGCCATTAAATAACTAAGTTGAGCGCTTACCCTCCTCTTC 3' (SEQ ID NO:10)
   3' TAAGGCGGGACACCCTAATAAAATATTCCAATTGTTTTTTTGCATAGGCGCGGTAATTTATTGATTCAACTCGCGAATGGGAGGAGAAG 5'

U  5' ATTCCGCCCTGTGGGATTATTTTATAAGGTTAACAAAAAAACATATCCACCATTAAATAACTAAGTTGAGCGCTTACCCTCCTCTTC 3' (SEQ ID NO:11)
   3' TAAGGCGGGACACCCTAATAAAATATTCCAATTGTTTTTTTGTATAGGTGGTAATTTATTGATTCAACTCGCGAATGGGAGGAGAAG 5'

Figure 7

```
MLH2O  ATTCCGCCCTGTGGGATTATuuuuATAAGGTT >>  (SEQ ID NO:13)                      CommR2G <<  ATTCAACTCGCCTTACCCTCCTCTTC 5'  (SEQ ID NO:12)
MLHF1  CCGCCCTGTGGGATTATTTTATAAGTTAACAAGTATCCGCGCCAAAG (SEQ ID NO:14)
                                                      ‾‾‾‾‾‾‾‾‾‾‾‾‾
    3' TAAGGCGGGACACCCTAATAAAAATATTCCAATTGTTTTTTGCATAGGCGCGGTAATTTATTGATTCAACTCGCGAATGGGAGGAGAAG 5'
                                                    ‾               ‾‾‾‾‾‾‾‾‾‾‾‾‾‾‾‾
    3' TAAGGCGGGACACCCTAATAAAAATATTCCAATTGTTTTTTGTATAGGTGTGGTAATTTATTGATTCAACTCGCGAATGGGAGGAGAAG 5'
                                                    ‾               ‾‾‾‾‾‾‾‾‾‾‾‾‾‾‾‾
```

Figure 8

TMEFF2 gene

Target region sequence
TTCCCAGAGCTCCCTCCTTATGGCAGCAGTTCTCAGCGGACGACGACCCTCTGCTCTCCGGGCTGAGCCAGTCCCTGAGATC
ATGCGCGGGTTTGctgctgcttccccgccggtgccactgccaccgccgccctctgtgccgccgtcCGCGGGATGCTCAGTAGCCGCTGCCGG (SEQ ID NO:15)

Forward priming region
5'->3' Target       ---GTTTTTTAGAGTTTTTTTTTATGGTAGTAGTTTTCGCGTTTTCGGCGTAGTTTTTAGCGGACGATTTTTCG--- (SEQ ID NO:16)
TMEFInL1               TTTTTAGAGTTTTTTTTTATGGTAGTAGTΔGTTTTT >> (SEQ ID NO:17)
TMEFLdS170             TGGCCCGTCCGCGTCCCTCTGTTTGCTGTΔTTCGCCGTTTTCGGCAA-ddG (SEQ ID NO:18)
MCD6                   TGG555GT5G55GT555T5GΔTTTGCT >> (SEQ ID NO:19)

Reverse priming region (bottom strand)
5'->3' Target       ---AAAACGGAACAACGAACTACTAAACATCCCGAACGACGACGAACAATAAACAACACCCGACGA--- (SEQ ID NO:20)
TMEFInR1               CCRAACAACRAACTACTAAΔCATCCC >> (SEQ ID NO:21)
TMEFRdS133             CACACGTCGCTCGGGCCTGTTCTTGTCAΔCCCGCGAACGACGA-ddG (SEQ ID NO:22)
MCD4                   CA5A5GT5G5T5GGG55TGTGΔTCTTGT >> (SEQ ID NO:23)

hMLH1 gene

Target region sequence
AATGCTATCAAAGAGATGATTGAGAACTGGTACGAGGAGTCGAGCCGGCTCACTTAAGCGGCCGCGTCACTCAATGGCGCGGACACGCCTCTTTGCCCGGGCAG
AGGCATGTACAG (SEQ ID NO:24)

Forward priming region
5'->3' Target       ---GCGGGTTAGTTAATGTTAATTAAAGAGATGATTGAGAATTGGTACGAGGAGTCGAGTCGGGTTTATTTAAGGGTTACGATTTAAC--- (SEQ ID NO:25)
MLHinit2               AATGTTATTAAAGAGATGATTGAGAΔTTGGTA >> (SEQ ID NO:26)
RMLH170                TGGCCCGTCGCCGTCCCTCTGTTTTGCTTTGΔTACGGAGGAGTCGCC-ddG (SEQ ID NO:27)
MCD6                   TGG555GT5G55GT555T5GΔTTTGCT >> (SEQ ID NO:19)

Reverse priming region (bottom strand)
5'->3' Target       ---TAAACATACGCTATACATACCTCTACCCGAACAAAAAACGTATCCGCCATTAAATAACGGACCCGTTAAATCGTAACCCT--- (SEQ ID NO:31)
MLHinit1               CTATACATACCTCTACCCGRAACAACAΔAAAAAC >> (SEQ ID NO:29)
131hMLHFoldS2          CACACGTCGCTCGGGCCTGTTCTTGTAAAAΔCGTATCCGGCCAGG-ddG (SEQ ID NO:30)
MCD4                   CA5A5GT5G5T5GGG55TGTGΔTCTTGT >> (SEQ ID NO:23)

Figure 10

SEQUENCE LISTING

<160> NUMBER OF SEQ ID NOS: 33

<210> SEQ ID NO 1

```
<211> LENGTH: 21
<212> TYPE: DNA
<213> ORGANISM: Artificial Sequence
<220> FEATURE:
<223> OTHER INFORMATION: synthetic Hybridisation Dependent Chain
      Reaction (HDCR) reverse primer AluRev

<400> SEQUENCE: 1
gcctcggcct cccaaagtgc t                                              21

<210> SEQ ID NO 2
<211> LENGTH: 79
<212> TYPE: DNA
<213> ORGANISM: Artificial Sequence
<220> FEATURE:
<223> OTHER INFORMATION: synthetic Hybridisation Dependent Chain
      Reaction (HDCR) target DNA template derived from human Alu
      repeat sequence
<220> FEATURE:
<221> NAME/KEY: modified_base
<222> LOCATION: (29)...(29)
<223> OTHER INFORMATION: n = abasic site (d-spacer, delta)

<400> SEQUENCE: 2
ggcgtcgtgg gcggtgtggg atggcgttna gtgttcggtg gctcacgcct gtaatcccag    60
cactttggga ggccgaggc                                                 79

<210> SEQ ID NO 3
<211> LENGTH: 35
<212> TYPE: DNA
<213> ORGANISM: Artificial Sequence
<220> FEATURE:
<223> OTHER INFORMATION: synthetic Hybridisation Dependent Chain
      Reaction (HDCR) forward initiator primer InAluPr3
<220> FEATURE:
<221> NAME/KEY: modified_base
<222> LOCATION: (29)...(29)
<223> OTHER INFORMATION: n = abasic site (d-spacer, delta)

<400> SEQUENCE: 3
ggcgtcgtgg gcggtgtggg atggcgttna gtgtt                               35

<210> SEQ ID NO 4
<211> LENGTH: 62
<212> TYPE: DNA
<213> ORGANISM: Artificial Sequence
<220> FEATURE:
<223> OTHER INFORMATION: synthetic Hybridisation Dependent Chain
      Reaction (HDCR) facilitator oligonucleotide InAluFol15
<220> FEATURE:
<221> NAME/KEY: modified_base
<222> LOCATION: (2)...(26)
<223> OTHER INFORMATION: n = i (inosine)
<220> FEATURE:
<221> NAME/KEY: modified_base
<222> LOCATION: (40)...(61)
<223> OTHER INFORMATION: n = abasic site (d-spacer, delta)

<400> SEQUENCE: 4
gncgtcntgn gcgntgtngg atngcnttta gtgttcggtn gctcacgcct gtaatccctn    60 ng                                                                   62

<210> SEQ ID NO 5
<211> LENGTH: 77
<212> TYPE: DNA
<213> ORGANISM: Artificial Sequence
<220> FEATURE:
<223> OTHER INFORMATION: synthetic Hybridisation Dependent Chain
      Reaction (HDCR) mutant V600E template sequence (MUTB) derived from
      v-raf murine sarcoma viral oncogene homolog B1 (BRAF)
```

```
<400> SEQUENCE: 5
cgacggtggg tggttgctgt gtcctgtgtc tacagagaaa tctcgatcct cttagaagag        60
gctaagcgga ggtcagg                                                      77

<210> SEQ ID NO 6
<211> LENGTH: 77
<212> TYPE: DNA
<213> ORGANISM: Artificial Sequence
<220> FEATURE:
<223> OTHER INFORMATION: synthetic Hybridisation Dependent Chain
      Reaction (HDCR) normal template sequence (NORB) derived from v-raf
      murine sarcoma viral oncogene homolog B1 (BRAF)

<400> SEQUENCE: 6
cgacggtggg tggttgctgt gtcctgtgtc tacagtgaaa tctcgatcct cttagaagag        60
gctaagcgga ggtcagg                                                      77

<210> SEQ ID NO 7
<211> LENGTH: 26
<212> TYPE: DNA
<213> ORGANISM: Artificial Sequence
<220> FEATURE:
<223> OTHER INFORMATION: synthetic Hybridisation Dependent Chain
      Reaction (HDCR) reverse primner CommR3G

<400> SEQUENCE: 7
cctgacctcc gcttagcctc ttctaa                                            26

<210> SEQ ID NO 8
<211> LENGTH: 54
<212> TYPE: DNA
<213> ORGANISM: Artificial Sequence
<220> FEATURE:
<223> OTHER INFORMATION: synthetic Hybridisation Dependent Chain
      Reaction (HDCR) facilitator oligonucleotide BFol3
<220> FEATURE:
<221> NAME/KEY: modified_base
<222> LOCATION: (2)...(16)
<223> OTHER INFORMATION: n = i (inosine)
<220> FEATURE:
<221> NAME/KEY: modified_base
<222> LOCATION: (54)...(54)
<223> OTHER INFORMATION: n = dideoxyguanosine (ddG)

<400> SEQUENCE: 8
cnacgntgnn tnnttnctgt gtcctgtgtc tacagagaaa tctcgatgga gaan             54

<210> SEQ ID NO 9
<211> LENGTH: 28
<212> TYPE: DNA
<213> ORGANISM: Artificial Sequence
<220> FEATURE:
<223> OTHER INFORMATION: synthetic Hybridisation Dependent Chain
      Reaction (HDCR) initiator primer BRF2
<220> FEATURE:
<221> NAME/KEY: modified_base
<222> LOCATION: (22)...(22)
<223> OTHER INFORMATION: n = abasic site (d-spacer, delta)

<400> SEQUENCE: 9
cgacggtggg tggttgctgt gnccgtgtg                                         28

<210> SEQ ID NO 10
<211> LENGTH: 90
<212> TYPE: DNA
<213> ORGANISM: Artificial Sequence
<220> FEATURE:
```

<223> OTHER INFORMATION: synthetic Hybridisation Dependent Chain
      Reaction (HDCR) methylated template (Template M) derived
      from hMLH1 gene

<400> SEQUENCE: 10
attccgccct gtgggattat ttttataagg ttaacaaaaa aacgtatccg cgccattaaa    60
taactaagtt gagcgcttac cctcctcttc                                    90

<210> SEQ ID NO 11
<211> LENGTH: 90
<212> TYPE: DNA
<213> ORGANISM: Artificial Sequence
<220> FEATURE:
<223> OTHER INFORMATION: synthetic Hybridisation Dependent Chain
      Reaction (HDCR) unmethylated template (Template U) derived
      from hMLH1 gene

<400> SEQUENCE: 11
attccgccct gtgggattat ttttataagg ttaacaaaaa aacatatcca caccattaaa    60
taactaagtt gagcgcttac cctcctcttc                                    90

<210> SEQ ID NO 12
<211> LENGTH: 26
<212> TYPE: DNA
<213> ORGANISM: Artificial Sequence
<220> FEATURE:
<223> OTHER INFORMATION: synthetic Hybridisation Dependent Chain
      Reaction (HDCR) reverse primer CommR3G

<400> SEQUENCE: 12
cttctcctcc cattccgctc aactta                                        26

<210> SEQ ID NO 13
<211> LENGTH: 32
<212> TYPE: DNA
<213> ORGANISM: Artificial Sequence
<220> FEATURE:
<223> OTHER INFORMATION: synthetic Hybridisation Dependent Chain
      Reaction (HDCR) initiator primer MLH2O
<220> FEATURE:
<221> NAME/KEY: modified_base
<222> LOCATION: (21)...(24)
<223> OTHER INFORMATION: n = um (2'-O-methyl uridine)

<400> SEQUENCE: 13
attccgccct gtgggattat nnnnataagg tt                                 32

<210> SEQ ID NO 14
<211> LENGTH: 55
<212> TYPE: DNA
<213> ORGANISM: Artificial Sequence
<220> FEATURE:
<223> OTHER INFORMATION: synthetic Hybridisation Dependent Chain
      Reaction (HDCR) facilitator oligonucleotide MLHF1
<220> FEATURE:
<221> NAME/KEY: modified_base
<222> LOCATION: (34)...(54)
<223> OTHER INFORMATION: n = abasic site (d-spacer, delta)

<400> SEQUENCE: 14
ccgccctgtg ggattatttt tataaggtta acancaaaac gtatccgcgc canng        55

<210> SEQ ID NO 15
<211> LENGTH: 220
<212> TYPE: DNA
<213> ORGANISM: Artificial Sequence
<220> FEATURE:
<223> OTHER INFORMATION: synthetic Hybridisation Dependent Chain -continued Reaction (HDCR) TMEFF2 target region sequence

<400> SEQUENCE: 15
ttcccagagc tccctcctta tggcagcagc ttcccgcgtc tccggcgcag cttctcagcg    60
gacgaccctc tcgctccggg gctgagccca gtccctggat gttgctgaaa ctctcgagat   120
catgcgcggg tttggctgct gcttccccgc cgggtgccac tgccaccgcc gccgcctctg   180
ctgccgccgt ccgcgggatg ctcagtagcc cgctgcccgg                         220

<210> SEQ ID NO 16
<211> LENGTH: 75
<212> TYPE: DNA
<213> ORGANISM: Artificial Sequence
<220> FEATURE:
<223> OTHER INFORMATION: synthetic Hybridisation Dependent Chain
      Reaction (HDCR) TMEFF2 forward priming region, 5'-3'
      target, priming site region

<400> SEQUENCE: 16 gtttttaga gttttttttt tatggtagta gttttttcgcg ttttcggcgt agttttttag    60
cggacgattt tttcg                                                     75

<210> SEQ ID NO 17
<211> LENGTH: 34
<212> TYPE: DNA
<213> ORGANISM: Artificial Sequence
<220> FEATURE:
<223> OTHER INFORMATION: synthetic Hybridisation Dependent Chain
      Reaction (HDCR) TMEFF2 initiator oligonucleotide TMEFInL2
<220> FEATURE:
<221> NAME/KEY: modified_base
<222> LOCATION: (28)...(28)
<223> OTHER INFORMATION: n = abasic site (d-spacer, delta)

<400> SEQUENCE: 17
tttttagagt ttttttttta tggtagtngt tttt                                34

<210> SEQ ID NO 18
<211> LENGTH: 49
<212> TYPE: DNA
<213> ORGANISM: Artificial Sequence
<220> FEATURE:
<223> OTHER INFORMATION: synthetic Hybridisation Dependent Chain
      Reaction (HDCR) TMEFF2 facilitator oligonucleotide
      TMEFLdS170
<220> FEATURE:
<221> NAME/KEY: modified_base
<222> LOCATION: (31)...(31)
<223> OTHER INFORMATION: n = abasic site (d-spacer, delta)
<220> FEATURE:
<221> NAME/KEY: modified_base
<222> LOCATION: (49)...(49)
<223> OTHER INFORMATION: n = dideoxyguanosine (ddG)

<400> SEQUENCE: 18
tggcccgtcg ccgtccctct gttttgctgt ntttcgcgtt ttcggcaan                49

<210> SEQ ID NO 19
<211> LENGTH: 28
<212> TYPE: DNA
<213> ORGANISM: Artificial Sequence
<220> FEATURE:
<223> OTHER INFORMATION: synthetic Hybridisation Dependent Chain
      Reaction (HDCR) common outer facilitator
      oligonucleotide-dependent primer MCD6
<220> FEATURE:
<221> NAME/KEY: modified_base
<222> LOCATION: (4)...(19)
<223> OTHER INFORMATION: c = 5-methyl cytosine (5)

-continued

```
<220> FEATURE:
<221> NAME/KEY: modified_base
<222> LOCATION: (22)...(22)
<223> OTHER INFORMATION: n = abasic site (d-spacer, delta)

<400> SEQUENCE: 19
tggcccgtcg ccgtccctct gntttgct                                              28

<210> SEQ ID NO 20
<211> LENGTH: 78
<212> TYPE: DNA
<213> ORGANISM: Artificial Sequence
<220> FEATURE:
<223> OTHER INFORMATION: synthetic Hybridisation Dependent Chain
      Reaction (HDCR) TMEFF2 reverse priming region (bottom
      strand), 5'-3' target, priming site region

<400> SEQUENCE: 20
aaaaccgaac aacgaactac taaacatccc gcgaacgacg acaacaaaaa cgacgacgat          60
aacaataaca cccgacga                                                        78

<210> SEQ ID NO 21
<211> LENGTH: 26
<212> TYPE: DNA
<213> ORGANISM: Artificial Sequence
<220> FEATURE:
<223> OTHER INFORMATION: synthetic Hybridisation Dependent Chain
      Reaction (HDCR) TMEFF2 initiator oligonucleotide TMEFInR1
<220> FEATURE:
<221> NAME/KEY: modified_base
<222> LOCATION: (20)...(20)
<223> OTHER INFORMATION: n = abasic site (d-spacer, delta)

<400> SEQUENCE: 21
ccraacaacr aactactaan catccc                                               26

<210> SEQ ID NO 22
<211> LENGTH: 47
<212> TYPE: DNA
<213> ORGANISM: Artificial Sequence
<220> FEATURE:
<223> OTHER INFORMATION: synthetic Hybridisation Dependent Chain
      Reaction (HDCR) TMEFF2 facilitator oligonucleotide
      TMEFRdS133
<220> FEATURE:
<221> NAME/KEY: modified_base
<222> LOCATION: (31)...(31)
<223> OTHER INFORMATION: n = abasic site (d-spacer, delta)
<220> FEATURE:
<221> NAME/KEY: modified_base
<222> LOCATION: (47)...(47)
<223> OTHER INFORMATION: n = dideoxyguanosine (ddG)

<400> SEQUENCE: 22
cacacgtcgc tcgggcctgt gttcttgtca ncccgcgaac gacggan                        47

<210> SEQ ID NO 23
<211> LENGTH: 28
<212> TYPE: DNA
<213> ORGANISM: Artificial Sequence
<220> FEATURE:
<223> OTHER INFORMATION: synthetic Hybridisation Dependent Chain
      Reaction (HDCR) common outer facilitator
      oligonucleotide-dependent primer MCD4
<220> FEATURE:
<221> NAME/KEY: modified_base
<222> LOCATION: (3)...(17)
<223> OTHER INFORMATION: c = 5-methyl cytosine
<220> FEATURE:
<221> NAME/KEY: modified_base
<222> LOCATION: (22)...(22)
```

<223> OTHER INFORMATION: n = abasic site (d-spacer, delta)

<400> SEQUENCE: 23
cacacgtcgc tcgggcctgt gntcttgt                                              28

<210> SEQ ID NO 24
<211> LENGTH: 133
<212> TYPE: DNA
<213> ORGANISM: Artificial Sequence
<220> FEATURE:
<223> OTHER INFORMATION: synthetic Hybridisation Dependent Chain
      Reaction (HDCR) hMLH1 target region sequence

<400> SEQUENCE: 24
aatgctatca aagagatgat tgagaactgg tacggaggga gtcgagccgg gctcacttaa           60
gggctacgac ttaacgggcc gcgtcactca atggcgcgga cacgcctctt tgcccgggca          120
gaggcatgta cag                                                             133

<210> SEQ ID NO 25
<211> LENGTH: 85
<212> TYPE: DNA
<213> ORGANISM: Artificial Sequence
<220> FEATURE:
<223> OTHER INFORMATION: synthetic Hybridisation Dependent Chain
      Reaction (HDCR) hMLH1 forward priming region, 5'-3' target,
      priming site region

<400> SEQUENCE: 25
gcggttagtt aatgttatta aagagatgat tgagaattgg tacggaggga gtcgagtcgg           60
gtttatttaa gggttacgat ttaac                                                85

<210> SEQ ID NO 26
<211> LENGTH: 32
<212> TYPE: DNA
<213> ORGANISM: Artificial Sequence
<220> FEATURE:
<223> OTHER INFORMATION: synthetic Hybridisation Dependent Chain
      Reaction (HDCR) hMLH1 initiator primer MLHInit2
<220> FEATURE:
<221> NAME/KEY: modified_base
<222> LOCATION: (26)...(26)
<223> OTHER INFORMATION: n = abasic site (d-spacer, delta)

<400> SEQUENCE: 26
aatgttatta aagagatgat tgaganttgg ta                                        32

<210> SEQ ID NO 27
<211> LENGTH: 49
<212> TYPE: DNA
<213> ORGANISM: Artificial Sequence
<220> FEATURE:
<223> OTHER INFORMATION: synthetic Hybridisation Dependent Chain
      Reaction (HDCR) hMLH1 facilitator oligonucleotide RMLH170
<220> FEATURE:
<221> NAME/KEY: modified_base
<222> LOCATION: (32)...(32)
<223> OTHER INFORMATION: n = abasic site (d-spacer, delta)
<220> FEATURE:
<221> NAME/KEY: modified_base
<222> LOCATION: (49)...(49)
<223> OTHER INFORMATION: n = dideoxyguanosine (ddG)

<400> SEQUENCE: 27
tggcccgtcg ccgtccctct gttttgcttt gntacggagg gagtcgccn                      49

<210> SEQ ID NO 28
<211> LENGTH: 79

```
<212> TYPE: DNA
<213> ORGANISM: Artificial Sequence
<220> FEATURE:
<223> OTHER INFORMATION: synthetic target DNA template complement
      derived from human Alu repeat sequence

<400> SEQUENCE: 28
gcctcggcct cccaaagtgc tgggattaca ggcgtgagcc accgaacact aaacgccatc    60
ccacaccgcc cacgacgcc                                                 79

<210> SEQ ID NO 29
<211> LENGTH: 30
<212> TYPE: DNA
<213> ORGANISM: Artificial Sequence
<220> FEATURE:
<223> OTHER INFORMATION: synthetic Hybridisation Dependent Chain
      Reaction (HDCR) hMLH1 initiator primer MLHInit1
<220> FEATURE:
<221> NAME/KEY: modified_base
<222> LOCATION: (24)...(24)
<223> OTHER INFORMATION: n = abasic site (d-spacer, delta)

<400> SEQUENCE: 29
ctatacatac ctctacccra acanaaaaac                                     30

<210> SEQ ID NO 30
<211> LENGTH: 49
<212> TYPE: DNA
<213> ORGANISM: Artificial Sequence
<220> FEATURE:
<223> OTHER INFORMATION: synthetic Hybridisation Dependent Chain
      Reaction (HDCR) hMLH1 facilitator oligonucleotide 131hMLHFoldS2
<220> FEATURE:
<221> NAME/KEY: modified_base
<222> LOCATION: (33)...(33)
<223> OTHER INFORMATION: n = abasic site (d-spacer, delta)
<220> FEATURE:
<221> NAME/KEY: modified_base
<222> LOCATION: (49)...(49)
<223> OTHER INFORMATION: n = dideoxyguanosine (ddG)

<400> SEQUENCE: 30
cacacgtcgc tcgggcctgt gttcttgtaa aancgtatcc gcgccaggn                49

<210> SEQ ID NO 31
<211> LENGTH: 84
<212> TYPE: DNA
<213> ORGANISM: Artificial Sequence
<220> FEATURE:
<223> OTHER INFORMATION: synthetic Hybridisation Dependent Chain
      Reaction (HDCR) hMLH1 reverse priming region, 5'-3' target,
      priming site region

<400> SEQUENCE: 31
taaacatacg ctatacatac ctctacccga acaaaaaaac gtatccgcgc cattaaataa    60
cgcgacccgt taaatcgtaa ccct                                           84

<210> SEQ ID NO 32
<211> LENGTH: 24
<212> TYPE: DNA
<213> ORGANISM: Artificial Sequence
<220> FEATURE:
<223> OTHER INFORMATION: synthetic TMEFF2 HEX Taqman probe TPEFMC
<220> FEATURE:
<221> NAME/KEY: modified_base
<222> LOCATION: (1)...(1)
<223> OTHER INFORMATION: a modified by hexachloro-6-carboxyfluorescein
      (HEX)
<220> FEATURE:
<221> NAME/KEY: modified_base
```

-continued

```
<222> LOCATION: (24)...(24)
<223> OTHER INFORMATION: t modified by 6-carboxytetramethylrhodamine
      (TAMRA)

<400> SEQUENCE: 32
aaattttcga gattatgcgc gggt                                            24

<210> SEQ ID NO 33
<211> LENGTH: 25
<212> TYPE: DNA
<213> ORGANISM: Artificial Sequence
<220> FEATURE:
<223> OTHER INFORMATION: synthetic hMLH1 HEX Taqman probe hMLH
<220> FEATURE:
<221> NAME/KEY: modified_base
<222> LOCATION: (1)...(1)
<223> OTHER INFORMATION: a modified by hexachloro-6-carboxyfluorescein
      (HEX)
<220> FEATURE:
<221> NAME/KEY: modified_base
<222> LOCATION: (25)...(25)
<223> OTHER INFORMATION: t modified by Black Hole Quencher 1 (BHQ1)

<400> SEQUENCE: 33
acgcgacccg ttaaatcgta accct                                           25
```

NUCLEIC ACID AMPLIFICATION

FIELD OF THE INVENTION

The present invention relates to methods for the selective amplification of specific nucleic acid sequences. Selectivity of amplification is achieved by using at least one modified oligonucleotide primer in conjunction with a corresponding facilitator oligonucleotide in a thermocyclic enzymatic amplification reaction. Selectivity is also provided by sequences located within the amplicon to which the facilitator oligonucleotide binds. The invention also relates to amplification product manipulation and uses of modified product generated in accordance with methods of the invention, such as the addition of 3' single strand sequence which can be used as a unique nucleotide sequence binding site.

BACKGROUND OF THE INVENTION

The polymerase chain reaction (PCR) is a technique for rapidly synthesizing a large number of copies of a defined segment of a nucleic acid molecule (see, for example, Mullis et al U.S. Pat. Nos. 4,683,195, 4,683,202 and 4,800,159). The PCR technique is extremely sensitive, theoretically requiring only a single nucleic acid molecule for amplification. PCR is an enzyme-mediated reaction typically incorporating a template molecule, a pair of oligonucleotide primers and a nucleic acid polymerase in a reaction medium comprised of the appropriate salts, metal cations, free nucleotides and pH buffering system. The PCR process is based on repeated cycles of denaturation of double stranded nucleic acid, followed by oligonucleotide primer annealing to the nucleic acid template, and primer extension by the polymerase. The oligonucleotide primers used in PCR are designed to anneal to opposite strands of the template molecule and are positioned to flank the target sequence to be amplified. As the primers are extended from their 3' ends by the polymerase, the extension products provide copies of the original target sequence which can in turn act as template molecules for further rounds of amplification. PCR amplification results in the exponential increase of discrete nucleic acid molecules to obtain the desired amount of amplified nucleic acid product, the length of which is defined by the 5' ends of the oligonucleotide primers.

While simple and specific in principle, PCR is prone to several types of unwanted artefacts that can be problematic to users and can compromise the selectivity and specificity of the technique. For example, non-specific amplification of fragments may result from one or both of the primers binding to a sequence(s) other than the target sequence, which can produce one or more fragments that are not the desired product. Non-specific binding of primers frequently occurs and can be due, for example, to alternate primer binding sequences being present in the target nucleotide sequence template, the presence of similar primer binding sequences on foreign contaminating molecules and/or sub-optimal primer sequence design. These non-specific nucleic acid products can be problematic especially when template nucleic acid containing the target sequence is present in few copies.

In some instances primers may bind to only partially complementary binding sites, and be extended even when a mismatch to the bound DNA is present at the 3' end of a primer (e.g. see Kwok et al. 1990, "Effects of primer template mismatches on the polymerase chain-reaction—human-immunodeficiency-virus type-1 model studies." *Nucleic Acids Research* 18(4): 999-1005).

Because of this, unwanted non-specific amplification can occur. When the strand of DNA resulting from mispriming is copied, a primer binding site is generated that fully matches the primer. Thus unwanted products can appear in a standard PCR that at both ends have binding sites that are completely complementary to the primers. Thus once this unwanted product is produced it is likely to be amplified with high efficiency. In other words, once mispriming has occurred, no further specificity is possible in a standard PCR. Although various types of probes can be used to specifically detect the wanted target, if too much non-specific amplification occurs, production of the desired product can be prevented or reduced to levels that are undetectable with the specific probe. This situation is most likely to occur in cases where the target of interest constitutes only a very small fraction of the total nucleic acid.

Non-specific amplification is also exacerbated when it occurs in the early rounds of the PCR cycle. Typically in existing PCR techniques, specificity due to the sequences of the primers is only achieved in early rounds of the PCR. Once a significant amount of product is generated, amplification proceeds at equal rates whether primers have extended from the intended sites flanking the target sequence or from non-specific amplicons arising from mispriming. That is, even where primers may have bound to and extension occurred from incorrect sites to which the primers have only partial complementarity, amplified non-specific products have the exact oligonucleotide primer binding sequence incorporated by virtue of the PCR technique, and these compete at equal efficiency with the nucleic acid template containing the target sequence for oligonucleotide primer binding in subsequent PCR cycles. In applications such as allele-specific PCR considerable care in primer design and considerable effort in technique optimisation are typically required to minimise mispriming.

In an attempt to limit the occurrence of non-specific product amplification, current PCR techniques may employ modified procedures aimed at increasing the specificity of primer binding to the target nucleic acid. This may involve, for example, altering the presence and concentration of different co-factors mediating the primer binding process or modifying the thermocycling of the PCR method. Alternatively, nested PCR may be utilized which involves two sets of primers used in two successive rounds of PCR. The first PCR amplification produces target and potentially non-specific products using the first set of primers, while the second PCR round uses new primers to amplify a secondary target within the first round target product in an effort to reduce the generation of non-specific product.

While existing PCR technique modifications improving primer binding specificity are useful, many require extensive trial and error which can be both time consuming and cumbersome. In addition, even after incorporating these techniques, non-specific products often remain which are inherently difficult to eliminate. Consequently, there is an ongoing need for improving PCR-based methodologies that allow for improved selective amplification of target nucleic acid sequences.

As with these methods, the new invention described here includes selectivity for sequences lying between the priming sites on the starting nucleotide sequence and can provide within a single reaction additional sequence specificity as is normally obtained using nested primers and two rounds of PCR.

SUMMARY OF THE INVENTION

The present invention is predicated on the inventor's surprising finding that the specificity of a PCR can be enhanced by the use of two modified oligonucleotides which each bind to the same end of a target sequence. One of these modified oligonucleotides (termed herein the "facilitator oligonucleotide") does not act as a primer, possessing a modification at or near the 3' terminus preventing extension. The facilitator oligonucleotide acts as a template for amplicon sequence regeneration and is not incorporated directly into any amplification product. The other modified oligonucleotide (termed herein the "initiator primer") is modified such that whilst polymerase-mediated 3' extension from the primer is possible, copying by the polymerase on the opposite strand is prevented. In particular embodiments, this primer may share sufficient sequence identity with the 5' region of the facilitator oligonucleotide such that the initiator primer binding site is regenerated following strand extension using the facilitator oligonucleotide thereby enabling the initiator primer to initiate further rounds of strand synthesis. In such instances the initiator primer is "facilitator oligonucleotide-dependent" as successful binding to the amplified nucleotide sequence template depends on the facilitator oligonucleotide acting as a template for the regeneration of the initiator primer binding site. In instances where there is insufficient sequence identity between the initiator primer and the 5' region of the facilitator oligonucleotide the method may employ an additional "facilitator oligonucleotide-dependent primer", modified such that the presence of the modification prematurely terminates complementary strand synthesis, and which primer shares sufficient sequence identity with the 5' region of the facilitator oligonucleotide such that strand synthesis using the facilitator oligonucleotide generates a facilitator oligonucleotide-dependent primer binding site thereby enabling the facilitator oligonucleotide-dependent primer to initiate further rounds of strand synthesis. In accordance with the present invention the combination of facilitator oligonucleotide and initiator primer and/or facilitator oligonucleotide-dependent primer may be employed at one or both ends of a target sequence to be amplified.

Embodiments of the present invention provide methods for the selective amplification of specific target nucleotide sequences within biological samples containing nucleic acid molecules. Such methods are herein also collectively referred to as hybridisation dependent chain reaction (HDCR).

According to a first aspect of the invention there is provided method for the selective amplification of a target nucleotide sequence located within a nucleic acid molecule, the method comprising:

contacting the nucleic acid molecule ("template" molecule) with
  (i) at least one facilitator oligonucleotide, wherein the facilitator oligonucleotide includes at least one modification at or near its 3' terminus such that 3' extension from the facilitator oligonucleotide is blocked, and
  (ii) two or more oligonucleotide primers, at least one of which is an initiator primer modified such that the presence of the modification prematurely terminates complementary strand synthesis,
wherein the facilitator oligonucleotide and the initiator primer bind to substantially the same or adjacent regions of the template nucleic acid molecule and the facilitator oligonucleotide further comprises sequences complementary to the target sequence 3' to the binding location of the initiator primer; and
carrying out thermocyclic, enzymatic amplification such that the specific target sequence is selectively amplified.

The method may comprise the steps of:
(a) denaturing the template nucleic acid molecule;
(b) contacting the denatured template nucleic acid molecule with the at least one initiator primer and initiating second strand synthesis therefrom, thereby introducing the modification from the initiator primer into the newly synthesised strand;
(c) denaturing the double-stranded molecules so generated and initiating reverse strand synthesis from a primer located at the opposite end of the target nucleotide sequence to that which the initiator primer binds, whereby reverse strand synthesis prematurely terminates due to the modification introduced in step (b);
(d) denaturing the newly synthesised double-stranded molecules, binding the facilitator oligonucleotide to the incomplete reverse strand generated in step (c) and initiating strand extension therefrom to thereby complete the reverse strand; and
(e) optionally repeating steps (a) to (d) for one or more additional cycles.

In an embodiment the 5' region of the facilitator oligonucleotide shares sufficient sequence identity with the initiator primer such that the initiator primer binding site is regenerated following strand extension initiated from the facilitator oligonucleotide thereby enabling the initiator primer to initiate further rounds of strand synthesis.

In an alternative embodiment the 5' region of the facilitator oligonucleotide shares insufficient sequence identity with the initiator primer such that the initiator primer binding site is not regenerated following strand synthesis initiated from the facilitator oligonucleotide.

In accordance with this alternative embodiment the method may further employ a facilitator oligonucleotide-dependent primer, modified such that the presence of the modification prematurely terminates complementary strand synthesis, which primer shares sufficient sequence identity with the 5' region of the facilitator oligonucleotide such that strand synthesis initiated from the facilitator oligonucleotide generates a facilitator oligonucleotide-dependent primer binding site thereby enabling the facilitator oligonucleotide-dependent primer to initiate further rounds of strand synthesis.

The method may be used to improve the specificity of amplification of a desired target sequence, concomitantly substantially reducing or eliminating the amplification of undesired non-target sequences.

The nucleic acid molecule may be present in any suitable biological sample, including for example, tissues, cells and/or extracts thereof. The nucleic acid molecule may be purified from the biological sample prior to carrying out the amplification method in accordance with the invention.

The nucleic acid molecule may be DNA or RNA or may comprise a combination of deoxyribonucleotides, ribonucleotides and/or analogues of natural nucleotides.

Typically, the at least one modification that blocks 3' extension of the facilitator oligonucleotide includes the incorporation of one or more non-extendible moieties or nucleotide analogues at or near the 3' terminus, for example, a single 3' terminal non-extendible base or base analogue, a combination of a 3' terminal non-extendible base and one or more nucleotide mismatches near the 3' terminus of the oligonucleotide, or the incorporation of abasic sites near the 3' terminus of the oligonucleotide. The non-extendible base may be selected from, for example, a 2', 3' dideoxynucleotide, a 3' C3, C18 or other length spacer, a 3' phosphorylated nucleotide, a "peptide nucleic acid" base, a "locked nucleic acid" (LNA)

base, a nucleotide amine derivative, uracil treated with Uracil DNA glycosylase, RNA or a 2' O-methyl nucleotide, or a combination of these.

The initiator primer and/or the facilitator oligonucleotide-dependent primer may be modified by the inclusion of, for example, one or more spacers, abasic sites or modified nucleotides such as 2'-O-methyl nucleotides. Typically the modification in the initiator primer and/or the facilitator oligonucleotide-dependent primer is located sufficiently near to the 3' terminus of the primer such that whilst the primer retains the ability to initiate 3' extension, when the extended product containing the modification within its primer sequence is copied, the complementary strand is prematurely truncated preventing primer binding in subsequent amplification cycles. For example, in particular embodiments, the modification may be located about 10 bases, 9 bases, 8 bases, 7 bases, 6 bases, 5 bases or 4 bases from the 3' terminus of the primer.

The 5' terminus of the facilitator oligonucleotide may coincide with or fall within the 5' terminus of the initiator primer and/or the facilitator oligonucleotide-dependent primer. Alternatively, the facilitator oligonucleotide may comprise additional 5' sequence. Such additional sequence may be used as, or may facilitate the attachment of a detectable tag or label.

In an embodiment, both primers (forward and reverse primers) are initiator primers. In this case, two facilitator oligonucleotides are employed, one of which binds to substantially the same or adjacent region of the template nucleic acid molecule as the forward initiator primer and the other binds to substantially the same or adjacent region of the template nucleic acid molecule as the reverse initiator primer.

Further, the method may employ two facilitator oligonucleotide-dependent primers, one of which binds to substantially the same or adjacent region of the template nucleic acid molecule as one facilitator oligonucleotide and the other binds to substantially the same or adjacent region of the template nucleic acid molecule as the other facilitator oligonucleotide.

According to a second aspect of the invention there is provided a method for improving the specificity of a thermocyclic enzymatic amplification reaction, the reaction utilizing at least two oligonucleotide primers flanking a target nucleotide sequence of interest located within a nucleic acid molecule, wherein at least one of said primers is modified such that the presence of the modification prematurely terminates complementary strand synthesis and the reaction further utilizes at least one non-priming facilitator oligonucleotide, wherein the facilitator oligonucleotide includes at least one modification at or near its 3' terminus such that 3' extension from the facilitator oligonucleotide is blocked, and wherein the facilitator oligonucleotide and the modified primer bind to substantially the same or adjacent regions of the template nucleic acid molecule and the facilitator oligonucleotide further comprises sequences complementary to the target sequence 3' to the binding location of the modified primer.

The specificity of the thermocyclic enzymatic amplification reaction is typically determined by the elimination of, or reduction in the amount of, amplification product not comprising the target nucleotide sequence of interest.

Methods carried out in accordance with the above aspects and embodiments may be used, for example, in DNA methylation analysis and/or in the diagnosis of, or predictor of susceptibility to, a disease or condition in a subject, which disease or condition is characterised by or associated with a variant genetic sequence. The variant sequence may comprise the addition, deletion or substitution of one or more nucleotides or a modification, such as altered methylation status, to one or more nucleotides.

Accordingly, a third aspect of the present invention provides a method for detecting a variant nucleotide sequence, the method comprising selectively amplifying a target nucleotide sequence located within a nucleic acid molecule and comprising the variant sequence, wherein the method comprises:

contacting the nucleic acid molecule ("template" molecule) with
  (i) at least one facilitator oligonucleotide, wherein the facilitator oligonucleotide includes at least one modification at or near its 3' terminus such that 3' extension from the facilitator oligonucleotide is blocked, and
  (ii) two or more oligonucleotide primers, at least one of which is an initiator primer modified such that the presence of the modification prematurely terminates complementary strand synthesis, wherein the facilitator oligonucleotide and the initiator primer bind to substantially the same or adjacent regions of the template nucleic acid molecule and the facilitator oligonucleotide further comprises 3' sequences complementary to the target sequence 3' to the binding location of the initiator primer and wherein said 3' sequences enable preferential binding of the facilitator oligonucleotide to the target nucleotide sequence comprising the variant sequence rather than to corresponding nonvariant sequence;

carrying out thermocyclic, enzymatic amplification such that the specific target sequence is selectively amplified; and comparing the nucleotide sequence of the amplified product with a sequence corresponding to the nonvariant target sequence, to detect the variant nucleotide sequence.

In an embodiment the 5' region of the facilitator oligonucleotide shares sufficient sequence identity with the initiator primer such that the initiator primer binding site is regenerated following strand extension initiated from the facilitator oligonucleotide thereby enabling the initiator primer to initiate further rounds of strand synthesis.

In an alternative embodiment the 5' region of the facilitator oligonucleotide shares insufficient sequence identity with the corresponding region of the initiator primer such that the initiator primer binding site is not regenerated following strand synthesis initiated from the facilitator oligonucleotide.

In accordance with this alternative embodiment the method may further employ a facilitator oligonucleotide-dependent primer, which primer shares sufficient sequence identity with the 5' region of the facilitator oligonucleotide such that strand synthesis initiated from the facilitator oligonucleotide generates a facilitator oligonucleotide-dependent primer binding site thereby enabling the facilitator oligonucleotide-dependent primer to initiate further rounds of strand synthesis.

The variant sequence may comprise the addition, deletion or substitution of one or more nucleotides or a modification, such as altered methylation status, to one or more nucleotides within the target sequence.

BRIEF DESCRIPTION OF THE DRAWINGS

The present invention is described herein, by way of non-limiting example only, with reference to the accompanying drawings.

FIG. 2: Sequences and binding positions of reverse primer (AluRev; SEQ ID NO:1), forward initiator primer (InAluPr3;

SEQ ID NO:3) and facilitator oligonucleotide (InAluFol15; SEQ ID NO:4) to target nucleic acid sequence template (SEQ ID NO:2) derived from the human Alu repeat sequence (and its complementary strand, SEQ ID NO:28). A represents an abasic site; I represents inosine. Sequences shown after UDG-treatment.

Figure 3:
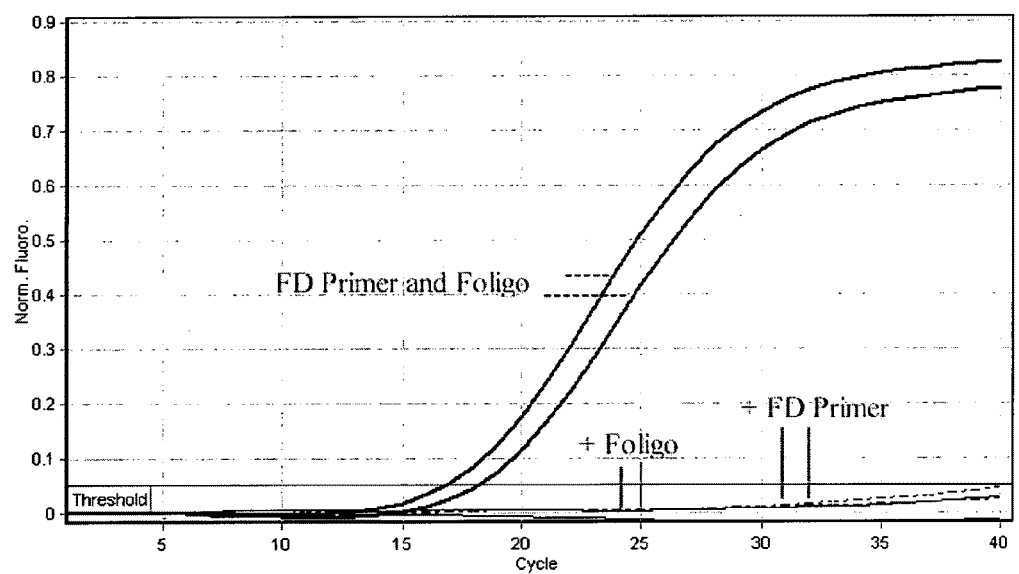

FIG. 3: Real-time HDCR amplification curves (in duplicate) showing the amount of amplified Alu product (measured by fluorescence) for hybridisation dependent chain reaction in accordance with an embodiment of the invention containing: initiator primer (FD primer) InAluPr3 alone; InAluFol15 facilitator oligonucleotide (foligo) alone; or FD primer InAluPr3 in combination with foligo InAluFol15.

FIG. 4: Sequence identity and alignment of mutant nucleic acid template sequence (MUTB; SEQ ID NO:5) and normal nucleic acid template sequence (NORB; SEQ ID NO:6). The oncogenic T to A mutation (V600E) is underlined in the mutant sequence (MUTB). The central region of the sequence shown (including the T to A mutation) is derived from the v-raf murine sarcoma viral oncogene homolog B1 (BRAF).

FIG. 5: Sequences and binding positions of reverse primer (CommR3G; SEQ ID NO:7), initiator primer (BRF2; SEQ ID NO:9) and facilitator oligonucleotide (BFol3; SEQ ID NO:8) to mutant (MUTB; SEQ ID NO:5 complement) and normal (NORB; SEQ ID NO:6 complement) target nucleic acid sequence template. Gaps in the underlined sequence represent target nucleic acid sequence mismatches to facilitator oligonucleotide (BFol3) or abasic site (Δ) in the initiator primer (BRF2). I represents inosine; ddG represents dideoxyguanosine.

Figure 6:
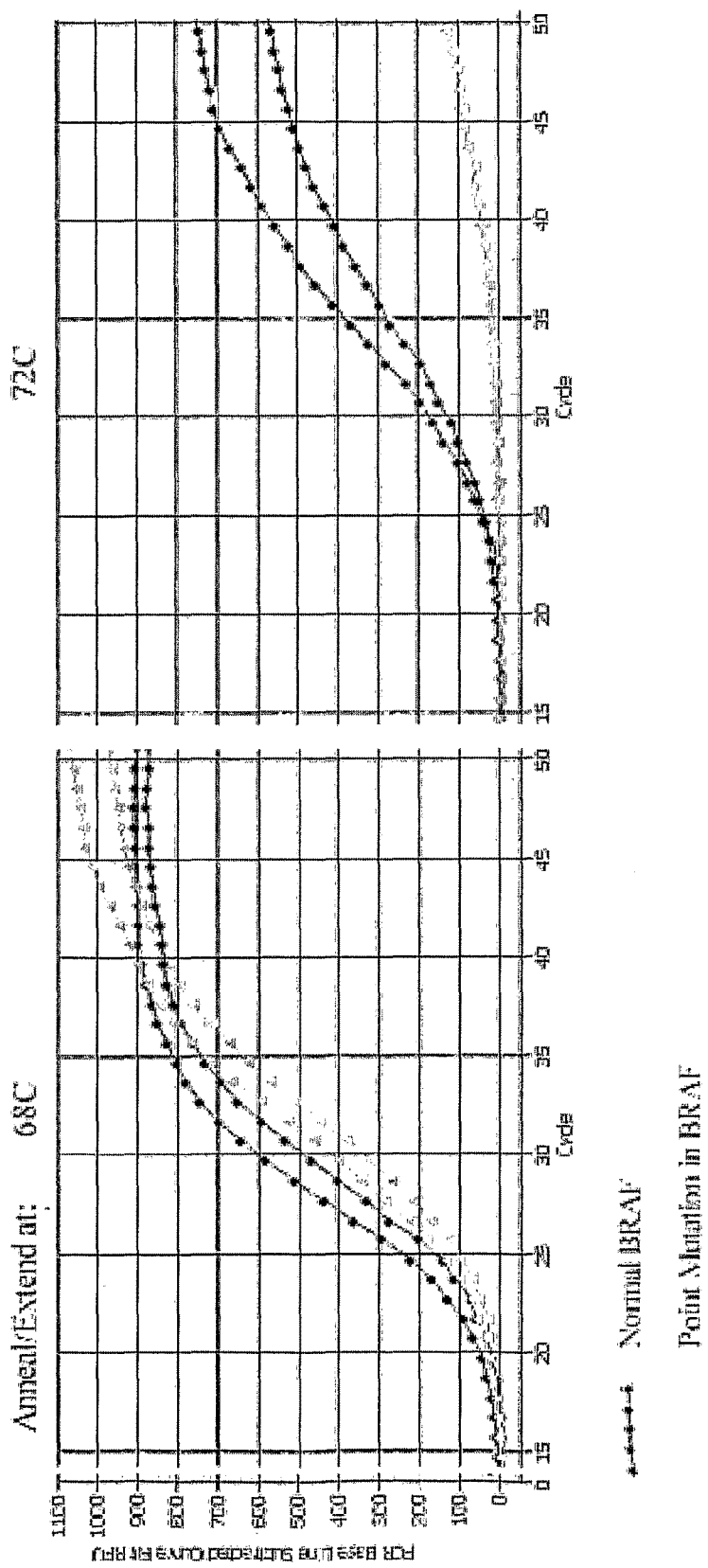

FIG. 6: Real-time HDCR amplification curves (in duplicate) showing the amount of amplified product (measured by fluorescence) as produced by hybridisation dependent chain reaction in accordance with an embodiment of the invention for normal BRAF gene target sequence (circles) and point mutation-containing BRAF gene target sequence (triangles), as shown in FIG. 4, at two annealing temperatures of 68° C. and 72° C.

FIG. 7: Sequence identity and alignment of methylated (M; SEQ ID NO:10) and unmethylated (U; SEQ ID NO:11) nucleotide sequence template derived from the hMLH1 gene. Underlined sequence indicates bisulphite treatment region of the hMLH1 gene, while regions in bold indicate residues that differ between M and U nucleotide sequence templates.

FIG. 8: Sequences and binding positions of reverse primer (CommR3G; SEQ ID NO:12), initiator primer (MLH2O; SEQ ID NO:13) and facilitator oligonucleotide (MLHF1; SEQ ID NO:14) to methylated (M; SEQ ID NO:10 complement) and unmethylated (U; SEQ ID NO:11 complement) target nucleic acid sequence template from the hMLH1 gene as shown in FIG. 7. Δ represents an abasic site (d-spacer); u represents 2'-O-methyl uridine. Underlined sequence indicates nucleotide differences between M and U sequence templates, with corresponding positions in the facilitator oligonucleotide also shown.

Figure 9:
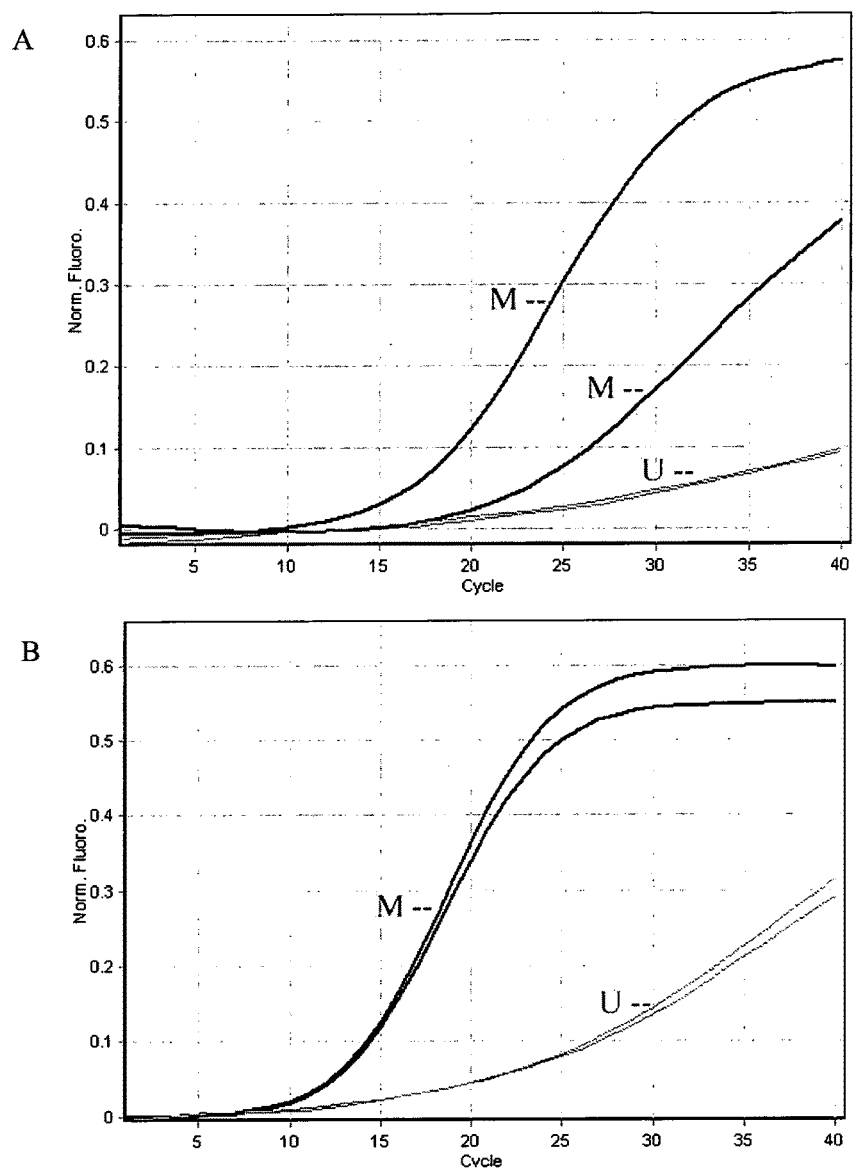

FIG. 9: A and B. Real-time HDCR amplification curves (each in duplicate) showing the effect of an intermediate thermocycling heating step (74° C.) (B) on the amount of amplified product (measured by fluorescence) from methylated (M) and unmethylated (U) target sequence templates from the hMLH1 gene.

FIG. 10: Target sequences of TMEFF2 (SEQ ID NO:15) and hMLH1 (SEQ ID NO:24) genes for amplification from bisulphite-treated DNA. Sequences arising from bisulphite conversion of the priming site regions (SEQ ID NOS:16, 20, 25 and 31) and the corresponding initiator oligonucleotides, TMEFInL1 (SEQ ID NO:17) and TMEFInR1 (SEQ ID NO:21) and facilitator oligonucleotides TMEFLdS170 (SEQ ID NO:18) and TMEFRdS133 (SEQ ID NO:22) for TMEFF2, initiator primers MLHInit2 (SEQ ID NO:26) and MLHInit1 (SEQ ID NO:29) and facilitator oligonucleotides RMLH170 (SEQ ID NO:27) and 131hMLHFoldS2 (SEQ ID NO:30) for hMLH1 and the common outer facilitator oligonucleotide-dependent primers MCD4 (SEQ ID NO:23) and MCD6 (SEQ ID NO:19) are aligned. ddG denotes a dideoxy G that was added using terminal transferase (post oligonucleotide synthesis). Underlined bases are mismatches that in conjunction with the added ddG reduce or eliminate extension. A indicates d-spacer; "5" indicates 5-methyl cytosine (when present in place of C in an oligonucleotide); and R indicates a mixture of A and G. The presence of further sequence is indicated by - - -.

Figure 11:
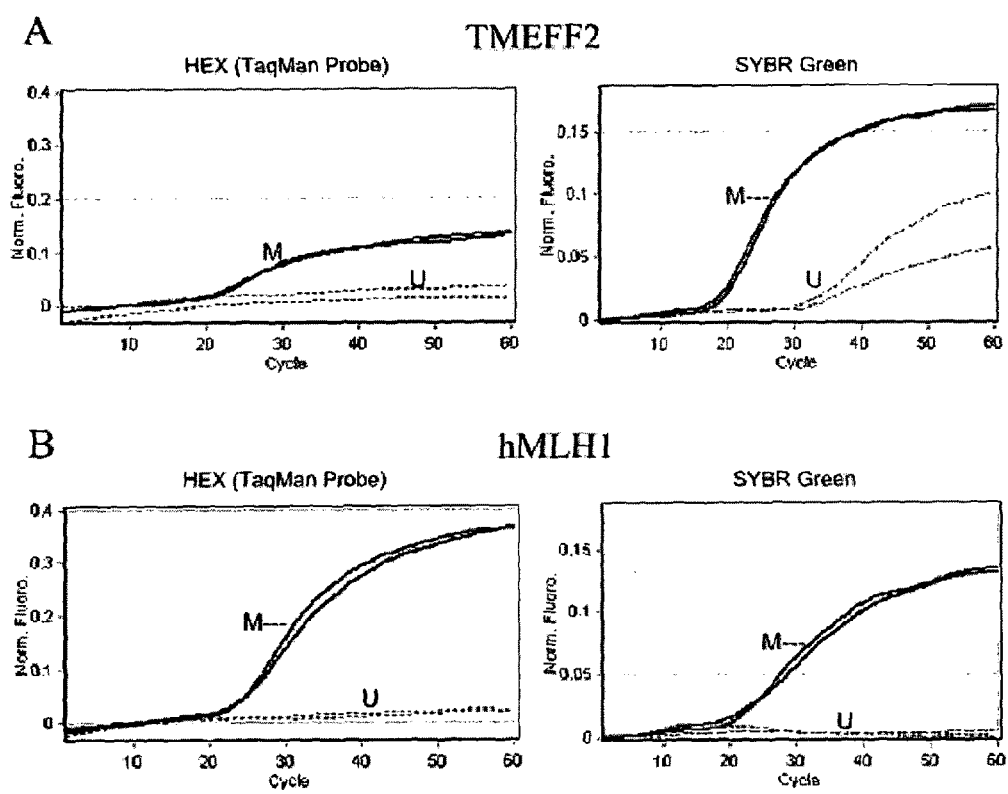

FIG. 11: Real-time HDCR amplification curves (each in duplicate) showing amplification of methylated TMEFF2 (Panel A) or hMLH1 (Panel B) from methylated (M) or unmethylated (U) bisulphite-treated template DNAs. In the left panels amplification of the methylated product was detected with specific HEX-labelled TaqMan probes and in the right panels total amplified DNA was detected using SYBR green.

Figure 12:
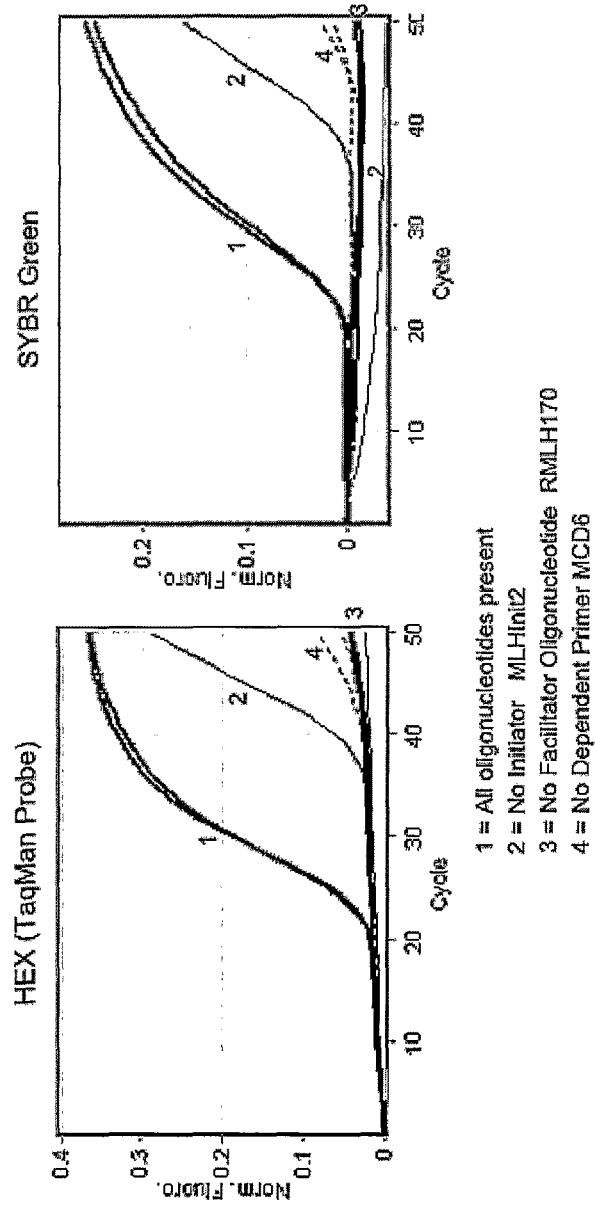

FIG. 12: Real-time HDCR amplification curves (each in duplicate) showing amplification of methylated hMLH1 from methylated, bisulphite-treated template DNA. Individual oligonucleotides were omitted as indicated. In the left panel amplification of the methylated product was detected with a specific HEX-labelled TaqMan probe and in the right panel total amplified DNA was detected using SYBR green.

DETAILED DESCRIPTION

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The articles "a" and "an" are used herein to refer to one or to more than one (i.e., to at least one) of the grammatical object of the article. By way of example, "an element" means one element or more than one element.

As used in the context of the present invention, the term "amplification" refers to making one or more copies of a targeted nucleotide sequence via a thermocyclic enzymatic reaction, and includes, but is not limited to the amplification of nucleic acid molecules by the polymerase chain reaction (PCR). As used herein the term "Polymerase Chain Reaction" (PCR) refers to a technique for producing a large number of copies of a specific segment of a nucleic acid sequence via oligonucleotide primer directed enzymatic amplification carried out in a thermocycling process. Examples of different PCR techniques include but are not limited to Reverse Transcription PCR, Nested PCR, Allele-Specific PCR, Quantitative PCR, Long Range PCR, Rapid Amplified Polymorphic DNA Analysis, Rapid Amplification of cDNA ends, Differential Display PCR, Ligation-Mediated PCR, Methylation specific PCR, Headloop PCR and Heavy Methyl PCR. PCR may refer to linear, non-exponential amplification of DNA in addition to exponential amplification of DNA, where the person skilled in the art would recognize that either form of amplification is appropriate for the purpose of the invention.

As used herein the terms "nucleic acid", "oligonucleotide" and "primer" designate any nucleic acid-based molecule, including DNA, cDNA, RNA, mRNA, cRNA, PNA or any combination thereof. Thus, a nucleic acid molecule, an oligonucleotide or a primer may comprise naturally occurring nucleotides, non-naturally nucleotides or a combination thereof.

As used herein the term "oligonucleotide" refers to a single-stranded sequence of deoxyribonucleotide or ribonucleotide bases, known analogues of natural nucleotides, or mixtures thereof. Oligonucleotides are typically short (for example less than 50 nucleotides in length) sequences which may be prepared by any suitable method, including, for example, direct chemical synthesis or cloning and restriction of appropriate sequences. Typically in the context of the present invention an oligonucleotide is designed to recognise and bind to a specific complementary nucleotide sequence located within a larger nucleic acid molecule. The oligonucleotide may or may not be able to act a primer for polymerase-mediated extension. Not all bases in an oligonucleotide need be complementary to the sequence to which the oligonucleotide is designed to bind; the oligonucleotide need only contain sufficient complementary bases to enable the oligonucleotide to recognise and bind to that sequence. An oligonucleotide may also include additional bases. The oligonucleotide sequence may be an unmodified nucleotide sequence or may be chemically modified or conjugated by a variety of means as described herein.

As used in the context of the present invention, the term "complementary strand synthesis" refers to the generation of complementary nucleotide sequence via an enzymatic reaction using denatured amplicon sequence as template.

As used herein the term "amplicon" refers to an amplified nucleotide sequence product incorporating at least one primer flanking the target sequence.

As used herein the term "primer" refers to an oligonucleotide which binds to a specific region of a single stranded template nucleic acid molecule and initiates nucleic acid synthesis via an enzymatic reaction, extending from the 3' end of the primer and complementary to the sequence of the template molecule. By convention, primers are typically referred to as 'forward' and 'reverse' primers, one of which is complementary to a nucleic acid strand and the other of which is complementary to the complement of that strand.

As used herein the term "target sequence" refers to a specific nucleotide sequence to be amplified. Oligonucleotides used in accordance with methods of the invention possess at least substantial sequence complementarity to nucleic acid sequences located at the 5' and 3' ends of the target sequence.

As used herein the term "at or near the 3' terminus" refers to the region of nucleotides immediately 5' of the 3' terminus and extending 5' of the 3' terminus of a nucleic acid molecule, typically including the terminal nucleotide.

As used in the context of the present invention, the term "blocked 3' extension" refers to the absence in practical terms of 3' extension of the facilitator oligonucleotide, such that the amplification reaction will not proceed, or proceeds at an unworkable rate.

As used herein, the term "substantially the same or adjacent regions" in the context of binding sites for facilitator oligonucleotides, and initiator primers and/or facilitator oligonucleotide-dependent primers means that the oligonucleotides/primers are capable of binding to the same general region of the template molecule, but not necessarily to the same nucleotide sequences of the template. For example, a facilitator oligonucleotide may bind to sequences of the template 3' to (downstream of) the sequences bound by an initiator primer, but still within substantially the same region of the template. In this case, the binding of the facilitator oligonucleotide occurs to sequences adjacent the binding sequences of the initiator primer. The term "adjacent" does not require that the sequences be immediately adjacent or 'abutting', but encompasses situations in which there are one or more intervening or overlapping nucleotides between 'adjacent' sequences.

As used herein the term "sample" refers to any biological sample that comprises nucleic acid molecules, typically comprising DNA and/or RNA. Samples may be tissues, cells or extracts thereof, or may be purified samples of nucleic acid molecules. Use of the term "sample" does not necessarily imply the presence of target sequence within nucleic acid molecules present in the sample.

Amplification methods of the present invention, also referred to herein collectively as Hybridisation Dependent Chain Reaction (HDCR), provide a high degree of specificity for any targeted nucleic acid amplification, which in turn dramatically reduces or eliminates non-specific amplification products.

The methodology described herein allows selection for the a desired target to be maintained for many cycles in the an amplification reaction, unlike in a standard prior art PCR. Even In the event that the efficiency of amplification of the desired target is only slightly better than that of unwanted products, the cumulative effect of maintaining this difference over a large number of cycles results in high selectivity for the desired target. This selectivity is achieved by using particular primers (referred to herein as 'initiator primers' and 'facilitator oligonucleotide-dependent primers') that contain a modification preventing them from being fully copied. No significant amplification is possible unless the primer binding sites can be regenerated to allow further binding and extension. Regeneration of a primer binding site is achieved using an oligonucleotide referred to herein as a facilitator oligonucleotide that is designed to recognize a sequence in the desired target, downstream of the initiator primer and/or facilitator oligonucleotide-dependent primer binding site. In the case of a mispriming event, this region is unlikely to sufficiently match the corresponding region in the facilitator oligonucleotide to allow regeneration of the primer binding site. Thus non-specific amplification can be reduced or eliminated. Furthermore, the system can be used to select for particular sequence variants such as mutations in the region downstream from the primer binding site. In this case, primer binding sites may be regenerated even when there is a mismatch with the facilitator oligonucleotide, but this occurs with lower efficiency and because selection can be maintained over a large number of cycles (depending upon the amount of target added to the reaction) a strong selection for the desired sequence variant can occur.

Prior art methodologies that also allow selection over a large number of cycles have also been described. These include the use of blocking oligonucleotides (as described for example in Cottrell et al. 2004, "A real-time PCR assay for DNA-methylation using methylation-specific blockers." Nucleic Acids Research 32(1)) and headloop DNA Amplification (described in US2005221312). In these methods, the improved specificity is due to the suppression of products with particular sequences. In cases where there may be many different unwanted potential products, multiple blocking oligonucleotides would need to be used to prevent unwanted amplification. Additionally, in the case of headloop DNA amplification, only one of the unwanted sequences can be selected against. By contrast, the present methodology described herein provides a positive selection for desired sequences and results in suppression of all unwanted products, even when the sequences of these products are unknown.

In PCR specificity of amplification depends on the specificity of binding of the primers and in prior art PCR methods specificity results from the design of appropriate forward and reverse primers with complementary sequence to the target sequence. However specificity due to the sequences of the primers is only achieved in early rounds of the PCR. Once a significant amount of product is generated amplification proceeds at equal rates whether primers have extended from the correct sites flanking the target sequence or from non-specific amplicons arising from mispriming.

In contrast, in the amplification methods of the invention selectivity is maintained in each cycle of the amplification. This high specificity is achieved by making amplification dependent upon the presence of the correct target sequence downstream of the priming region of one or both forward and reverse primers. Methods of the invention utilise at least one modified oligonucleotide primer at one (or both) ends of the target sequence with a corresponding facilitator oligonucleotide to increase the specificity of amplification. In the broadest form of the methodology described herein the modified primer is termed herein an initiator primer which is modified in such a way that reverse strand synthesis is impeded by the modification. The mispriming of prior art PCR methods which results in unwanted amplification products is avoided in methods of the present invention because the facilitator oligonucleotide will not recognise the nucleotide sequence located downstream (3') to the site of mispriming.

Accordingly, an aspect of the present invention provides a method for the selective amplification of a target nucleotide sequence located within a nucleic acid molecule, the method comprising:

contacting the nucleic acid molecule ("template" molecule) with
(i) at least one facilitator oligonucleotide, wherein the facilitator oligonucleotide includes at least one modification at or near its 3' terminus such that 3' extension from the facilitator oligonucleotide is blocked, and
(ii) at least two oligonucleotide primers, at least one of which is an initiator primer modified such that the presence of the modification prematurely terminates complementary strand synthesis, wherein the facilitator oligonucleotide and the initiator primer bind to substantially the same or adjacent regions of the template nucleic acid molecule and the facilitator oligonucleotide further comprises sequences complementary to the target sequence 3' to the binding location of the initiator primer; and carrying out thermocyclic, enzymatic amplification such that the specific target sequence is selectively amplified.

In accordance with embodiments of the invention, selectivity is maintained in every cycle of the amplification. Specificity results not only from the primer binding but also from the need to have the 'correct' sequence downstream of the primer binding site. As such, a surprisingly high degree of selectivity is maintained particularly if amplification incorporates more than one modified primer and facilitator oligonucleotide, whereby the generation of unwanted products resulting from mispriming are greatly reduced or eliminated.

The 5' region of the facilitator oligonucleotide may share sufficient sequence identity with the initiator primer such that the initiator primer binding site is regenerated following strand extension initiated from the facilitator oligonucleotide thereby enabling the initiator primer to initiate further rounds of strand synthesis. Alternatively, there may be insufficient sequence similarity between the 5' region of the facilitator oligonucleotide and the initiator primer such that the initiator primer binding site is not regenerated following strand synthesis using the facilitator oligonucleotide as template. In this latter case, the method will typically further employ a facilitator oligonucleotide-dependent primer, modified such that the presence of the modification prematurely terminates complementary strand synthesis, and which shares sufficient sequence identity with the 5' region of the facilitator oligonucleotide such that strand synthesis using the facilitator oligonucleotide generates a facilitator oligonucleotide-dependent primer binding site thereby enabling the facilitator oligonucleotide-dependent primer to initiate further rounds of strand synthesis.

A further aspect of the invention provides a method for improving the specificity of a thermocyclic enzymatic amplification reaction, the reaction utilizing at least two oligonucleotide primers flanking a target nucleotide sequence of interest located within a nucleic acid molecule, wherein at least one of said primers is modified such that the presence of the modification prematurely terminates complementary strand synthesis and the reaction further utilizes at least one non-priming facilitator oligonucleotide, wherein the facilitator oligonucleotide includes at least one modification at or near its 3' terminus such that 3' extension from the facilitator oligonucleotide is blocked, and wherein the facilitator oligonucleotide and the modified primer bind to substantially the same or adjacent regions of the template nucleic acid molecule and the facilitator oligonucleotide further comprises sequences complementary to the target sequence 3' to the binding location of the modified primer.

Methods of the invention may be used to improve the specificity of amplification of any desired target sequence, concomitantly substantially reducing or eliminating the amplification of undesired non-target sequences. Those skilled in the art will appreciate that the method may be used in any thermocyclic, enzymatic amplification reaction in which specificity and selectivity of amplification of a particular amplicon is desired.

By way of example only, methods of the present invention find application in DNA methylation analysis such as in methylation-specific PCR techniques improving the specificity of detection of methylated nucleotides. Methods of the invention also find application in the detection of point mutations, for example in disease diagnosis. In some instances a number of different point mutations may be associated with a particular disease (such as oncogenic mutations in the K-ras gene) requiring multiplexing of PCR. Methods of the invention are amenable to multiplexing. Those skilled in the art will appreciate that methods of the invention are not so limited in their application and the methods can be utilised in any thermocyclic enzymatic amplification requiring a high degree of selectivity and specificity. Such applications include, but are not limited to detection of pathogenic organisms including viruses and bacteria, detection of polymorphisms and/or mutations in genomes, genetic fingerprinting, forensic anthropology, molecular systematics, genealogical investigations, inherited disease detection, genome sequencing, identifying genes controlling traits of interest and detecting different states of DNA methylation.

Those skilled in the art will readily appreciate that any suitable means of blocking 3' extension from the 3' terminus of the facilitator oligonucleotide may be employed. Suitable blocking modifications include but are not limited to the incorporation of one or more non-extendible moieties or nucleotide analogues at or near the 3' terminus, for example, a single 3' terminal non-extendible base or base analogue, a combination of a 3' terminal non-extendible base and one or more nucleotide mismatches near the 3' terminus of the oligonucleotide, or the incorporation of abasic sites near the 3' terminus of the oligonucleotide. The non-extendible base may be selected from, for example, a 2', 3' dideoxynucleotide, a 3' C3, C18 or other length spacer, a 3' phosphorylated nucleotide, a "peptide nucleic acid" base, a "locked nucleic acid" (LNA) base, a nucleotide amine derivative, uracil treated with Uracil DNA glycosylase, RNA or a 2' O-methyl nucleotide, or a combination of these.

Similarly, a variety of suitable modifications can be employed in the facilitator oligonucleotide primer to terminate reverse strand synthesis. For example, these modifications may include, but are not limited to, the inclusion of one or more mismatches, abasic sites and/or modified nucleotides such as 2'-O-methyl nucleotides. Typically the modification in the initiator primer and/or the facilitator oligonucleotide-dependent primer is located sufficiently near to the 3' terminus of the primer such that whilst the primer retains the ability to initiate 3' extension, when the primer acts as a template for complementary strand synthesis, the amplified sequence product is truncated which results in lack of primer binding in subsequent amplification cycles. For example, in particular embodiments, the modification may be located about 10 bases, 9 bases, 8 bases, 7 bases, 6 bases, 5 bases or 4 bases from the 3' terminus of the primer.

The facilitator oligonucleotide comprises sequences complementary to the target nucleic acid sequence downstream from the initiator primer and/or facilitator oligonucleotide-dependent primer binding site. The facilitator oligonucleotide may also comprise sequences complementary to target sequences that are also recognised and bound by the initiator primer and/or facilitator oligonucleotide-dependent primer. The 5' end of the facilitator oligonucleotide may coincide or fall within with the 5' end of the initiator primer and/or facilitator oligonucleotide-dependent primer, or may contain a 5' extension of unique sequence that can be used to generate a unique sequence binding site for a tag on the amplified product if so desired. Such a tag binding site maybe used, for example, for the capture or detection of specific amplicons (for example mutation detection) or for cloning amplification products.

Figure 1A:
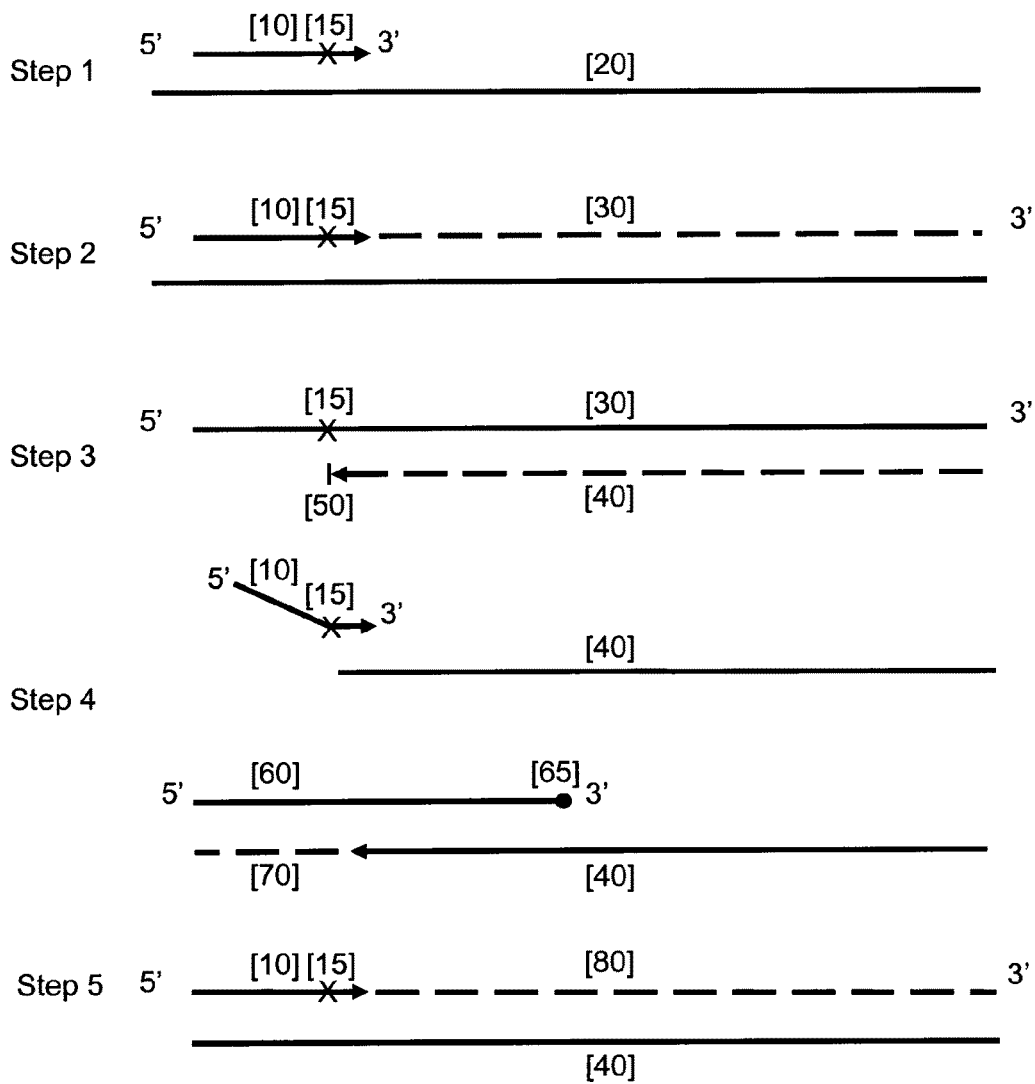
FIG. 1: Schematic representation of steps in a hybridisation dependent chain reaction in accordance with an embodiment of the invention.

By way of example only and without limiting the scope of the invention, typical steps of an amplification reaction carried out in accordance with an embodiment of the present invention are shown in FIG. 1A. Note that for simplicity only one end of the target nucleotide sequence participating in the amplification reaction is depicted in FIG. 1A. This figure shows schematically the roles of the initiator primer (10) (herein a 'forward' PCR primer) and facilitator oligonucleotide (60) in an embodiment of the invention. At the end of the target nucleotide sequence not shown in FIG. 1A, any suitable reverse primer may be utilised or alternatively a second initiator primer and corresponding second facilitator oligonucleotide may be employed.

Returning to the schematic of FIG. 1A, after an initial step of denaturing double stranded template sequence, the reaction is cooled to allow the initiator primer (10) to bind to complementary sequence on the single-stranded template (20) (Step 1). The initiator primer (10) includes a modification (15) at or near the 3' end of the primer. Forward strand synthesis is initiated from the 3' end of the initiator primer (Step 2) thereby generating a new nucleic acid strand (30). Following a second denaturation step, reverse strand synthesis (40) is initiated by the reverse primer (not shown) with the newly synthesised strand (30) incorporating the initiator primer as template (Step 3). However, synthesis of the reverse strand (40) is terminated prematurely (50) as copying is blocked by the presence of the modification (15) present in the new template, as provided by the initiator primer (10). Following a subsequent denaturation step, the facilitator oligonucleotide (60) hybridises preferentially over the initiator primer (10) to the incomplete reverse strand (40) generated in step 3 by virtue of greater sequence binding capacity of the 3' end of the facilitator oilgonucleotide (60) compared to the 3' end of the initiator primer (10) (Step 4). The facilitator oligonucleotide (60) includes a modification (65) at or near the 3' end of the oligonucleotide. The facilitator oligonucleotide (60) then acts as a template for extension on the reverse strand (40) such that completion of the reverse strand (70) and regeneration of the full binding site for the initiator primer is achieved (Step 4). At this point there is an optional step of heating the reaction to a temperature that will displace the facilitator oligonucleotide (60) from the template (40) without denaturing most or all of the full length double-stranded material. The reaction is then cooled to allow initiator primer (10) binding and a further round of forward strand (80) synthesis (Step 5).

Figure 1B:
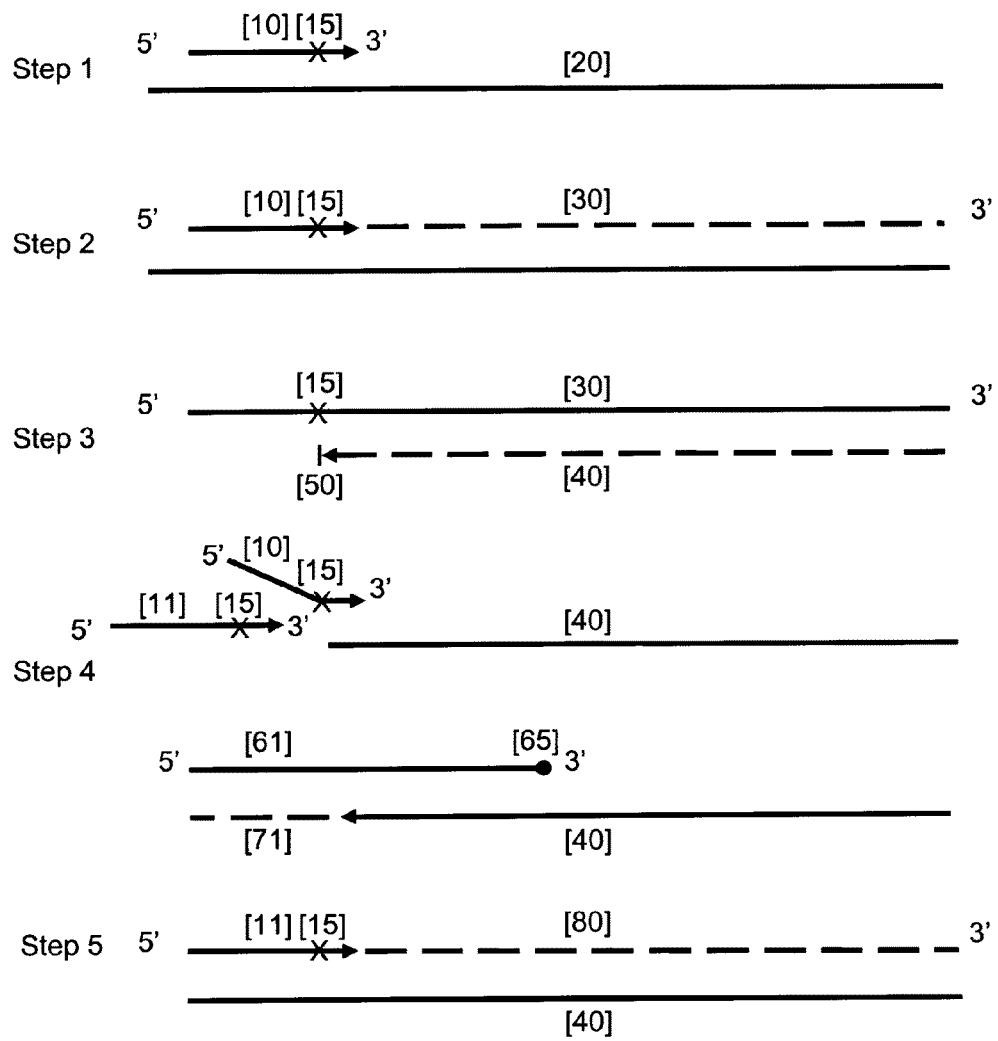

An alternative embodiment is exemplified in FIG. 1B. After an initial step of denaturing double stranded template sequence, the reaction is cooled to allow the initiator primer (10) to bind to complementary sequence on the single-stranded template (20) (Step 1). The initiator primer (10) includes a modification (15) at or near the 3' end of the primer. Forward strand synthesis is initiated from the 3' end of the initiator primer (Step 2) thereby generating a new nucleic acid strand (30). Following a second denaturation step, reverse strand synthesis (40) is initiated by the reverse primer (not shown) with the newly synthesised strand (30) incorporating the initiator primer as template (Step 3). However, synthesis of the reverse strand (40) is terminated prematurely (50) as copying is blocked by the presence of the modification (15) present in the new template, as provided by the initiator primer (10). Following a subsequent denaturation step, a facilitator oligonucleotide (61) that has a 5' region that is substantially similar to a facilitator oligonucleotide-dependent primer (11) hybridises preferentially over both the initiator and facilitator oligonucleotide primer to the incomplete reverse strand (40) generated in step 3 by virtue of greater sequence binding capacity of the 3' end of the facilitator oligonucleotide (61) compared to either the initiator primer (10) or the facilitator oligonucleotide-dependent primer (11) (Step 4). The facilitator oligonucleotide (61) includes a modification (65) at or near the 3' end of the oligonucleotide. The facilitator oligonucleotide (61) then acts as a template for extension on the reverse strand (40) such that completion of the reverse strand (71) and regeneration of the full binding site for the facilitator oligonucleotide-dependent primer is achieved (Step 4). At this point there is a preferred step of heating the reaction to a temperature that will displace the facilitator oligonucleotide (61) from the template (40) without denaturing any full length double-stranded material. The reaction is then cooled to allow facilitator oligonucleotide-dependent primer (11) binding and a further round of forward strand (80) synthesis (Step 5). It will be appreciated by those skilled in the art that the modification (15) in the initiator primer and the modification (15) in the facilitator oligonucleotide-dependent primer may be the same or different.

Forward strand synthesis using amplicon template sequence requires that the initiator primer or facilitator oligonucleotide-dependent primer anneals to the fully synthesised reverse strand following the regeneration of the 3' end of the reverse strand by the facilitator oligonucleotide. During this stage of the amplification cycle, competition in sequence binding between the initiator primer or facilitator oligonucleotide-dependent primer and the facilitator oligonucleotide is preferably minimised. In one embodiment, binding of the initiator primer or facilitator oligonucleotide-dependent primer can be favoured over binding of the facilitator oligonucleotide by using a low concentration of facilitator oligonucleotide and/or by incorporating modifications in the oligonucleotide sequence. For example, the binding of the initiator primer or facilitator oligonucleotide-dependent primer can be enhanced by use of modifications in the primer sequence known to those skilled in the art such as 5 methyl cytosine instead of cytosine, use of INAs or PNAs or attachment at the 5' terminus of a minor groove binder. In addition, the stability of facilitator oligonucleotide sequence binding can be reduced by the use of alternative bases such as inosine or deaza guanine instead of guanine.

In another embodiment, if the target sequence has a sequence alteration (eg., mutation) that is to be specifically amplified, this can be achieved by making the amplification dependent on the sequence-specific hybridization of a facilitator oligonucleotide to this region. This principle can be applied for detection of mutations and for selective amplification of differentially methylated DNA after bisulphite treatment for example. Even if only a relatively small selectivity is achieved in a single step of amplification, because this selectivity occurs over the whole period of the amplification, selectivity is significantly enhanced over the course of the reaction.

In a further embodiment, use of methods of the invention enable manipulations such as additions and/or extensions to be incorporated into the amplification products. For example, when the 5' tail on the facilitator oligonucleotide is made to be longer than 3' end of the amplicon template sequence incorporating the initiator primer or facilitator oligonucleotide-dependent primer, the final amplification product will have a 3' single strand extension. This sequence extension can then be used, for example, as a unique sequence binding site for primer/probe binding and/or attaching the amplification product to different substrates.

Typically the nucleic acid molecules to be analysed in accordance with the invention comprise DNA. However those skilled in the art will readily appreciate that methods of the present invention are also applicable to other nucleic acid molecules, such as RNAs, with the provision of the appropriate reagents, for example, RNA polymerases or reverse transcriptases, appropriate for amplification or copying of RNA.

As with other amplification methods, conditions such as annealing times, extension times, number of amplification cycles and temperatures employed in methods of the present invention are dependent on specific sequences and require individual optimization. Such optimization is within the skills and capabilities of those skilled in the art and require no more than mere routine experimentation (see for example Sambrook, J. and Russell, D. W. *Molecular Cloning: A Laboratory Manual*, Cold Spring Harbor Laboratory Press, 3rd Edition, 2001, and Dieffenbach, C. W. and Dveksler, G. S. (eds.) *PCR Primer: A Laboratory Manual*, Cold Spring Harbor Laboratory Press, 2nd Edition, 2003; the disclosures of which are incorporated herein by reference in their entirety). Additionally, methods of the invention may utilise any suitable enzyme capable of catalysing the synthesis of nucleotide sequence as a primer extension product. A variety of polymerases are available and suitable for use in accordance with the invention and such polymerases are known to those skilled in the art. In particular embodiments the polymerase is a DNA polymerase. The DNA polymerase may be selected, for example, from the group including *E. coli* DNA polymerase I, Klenow fragment of *E. coli* DNA polymerase I, T4 DNA polymerase, T7 DNA polymerase, *T. litoralis* DNA polymerase, and thermostable polymerases such as Taq, Tth, Pfu, Vent, deep vent, and UITma polymerases, and variations and derivatives thereof. As with other methods in which a common sequence is added to the ends of nucleic acid molecules to be amplified, amplification methods of the present invention can be readily adapted for multiplex PCR.

Products of amplification reactions carried out in accordance with the present invention may be detected by standard methods well known to those skilled in the art including, but not limited to, gel electrophoresis, real time monitoring using non-specific nucleic acid binding dyes such as SYBR Green, sequence specific fluorescent probes or hybridisation to arrays.

Those skilled in the art will appreciate the limitations associated with oligonucleotide primer design in standard PCR methodology. Similar limitations also apply to the design of oligonucleotide probes that may be used in the detection of PCR amplicons. Probes typically have to be designed to be able to hybridize better than the primers so that the probe is able to bind to single stranded target. Thus probes usually have to be long or have modifications to allow them to bind at a relatively high temperature compared to the primers. In order to use shorter probes, modifications to the PCR have to be made to allow the production of single stranded nucleic acid molecules in the PCR-exponential amplification only occurs for a limited number of cycles, followed by linear amplification. This is typically achieved by limiting the concentration of one of the primers, or by using primers of different binding temperatures and utilizing an increase in annealing temperature during the PCR. These limitations can be overcome using the amplification method in accordance with an embodiment of the invention which allows exponential amplification using 3' single strand tags—fluorescent probes can be used to bind to these regions after the extension phase. In addition, after an extension phase (eg., 72° C.), oligonucleotide probe binding at selected temperatures (eg., 40° C., 50° C. and 60° C.) can be measured. By combining different fluorescent dyes with different melting probe/tag combinations, multiplexing of a large number of reactions can be achieved. Alternatively, novel detection technology can be developed using the tag binding sites. In accordance with an embodiment of the invention, the presence of a 3' extension allows for the development, for example, of molecular beacon-like probes that will only fluoresce if they are copied by extension of the 3' single strand tag. Those skilled in the art will appreciate that the specific sequences of suitable facilitator oligonucleotides, initiator primers and facilitator oligonucleotide-dependent primers are required to be optimised depending on the sequence of the target nucleic acid sequences and the particular application in which the method will be used. The design of suitable oligonucleotide and primer sequences is well within the capabilities of those skilled in the art and require no more than mere routine experimentation.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Methods and Materials
Modified Oligonucleotide Primers
Examples of primer modifications which terminate primer extension are as follows: 2'-O methyl nucleotides—lower case (eg. u for 2' O methyl uridine), Inosine—I, Abasic sites—Δ, and/or +ddG—dideoxyguanosine added to end of oligonucleotide using terminal transferase. Abasic sites were included either by incorporation of a d-spacer during oligonucleotide synthesis or deoxy uridine. In the latter case uracils were converted to abasic sites by treating the oligonucleotide at 5 μM (i.e 1 nmole) with 4 units of Uracil-DNA Glycosylase (New England Biolabs) in 200 μL of TEX buffer (10 mM Tris HCl, 0.1 mM EDTA, 0.01% Triton-X100) for 2 hours at 37° C.

Nucleotide Sequence Template

Nucleotide target sequence template was prepared from synthetic single-stranded nucleic acid molecules corresponding to the target regions. Standard PCR amplification was used to amplify and generate double-stranded target sequence template. Amplification products were then diluted 1 in 10,000 and used as target region templates for HDCR amplification.

Amplification Conditions

Standard conditions for HDCR (in 25 μl) were conducted as follows: 1× Platinum Taq buffer [20 mM Tris-HCl (pH 8.4) and 50 mM KCl], 4 mM $MgCl_2$, 0.2 mM of each dNTP, 1/25,000 dilution of SYBR Green and 0.5 U Platinum Taq DNA polymerase (hot start) from Invitrogen, with oligonucleotide concentrations and cycling conditions specified in each example.

Example 1

Dependency on Initiator Primer and Facilitator Oligonucleotide for Successful Amplification This example demonstrates that the HDCR amplification technique in accordance with the embodiment of this invention depends upon the presence of both the initiator primer and the facilitator oligonucleotide.

HDCR was used to amplify a region of the human Alu repeat sequence as shown in FIG. 2. The effect of omitting either the initiator primer or facilitator oligonucleotide is shown. All reactions were done in duplicate. FIG. 2 shows the sequence of the target region, the initiator primer InAluPr3, the facilitator oligonucleotide InAluFol5 and the reverse primer AluRev. The initiator primer contains an abasic site and the 3' end of the facilitator oligonucleotide contains two abasic sites and two mismatches within the target nucleic acid sequence (T/T mismatch and a G/T mismatch) to prevent it priming. The facilitator oligonucleotide also contains an additional abasic site to reduce background caused by mispriming on the facilitator oligonucleotide.

Replicate amplifications containing 1 μL of a 1:10,000 dilution of nucleic acid template were performed in a Corbett Rotor-Gene 3000 Real-time PCR machine. Initiator primer InAluPr3 and facilitator oligonucleotide InAluFol5 were used at a concentration of 200 nM and the reverse primer AluRev at 40 nM. The thermocycling conditions were as follows: 95° C. for 2 minutes followed by 40 cycles of 95° C. for 1 second, 60° C. for 20 seconds, 80° C. for 1 second and 60° C. for 20 seconds. SYBR Green fluorescence was measured at the final 60° C. step. As indicated in FIG. 3, the initiator primer and facilitator oligonucleotide amplification product is observed after approximately 17 cycles, while the separate initiator primer or facilitator oligonucleotide reactions have not yet passed the detection threshold at 40 cycles.

Example 2

Selective Amplification Using HDCR Methodology

This example demonstrates that it is possible to achieve selective amplification from nucleic acid templates differing by a single base pair. The central region of the sequence shown in FIG. 4 corresponds to part of the sequence of the v-raf murine sarcoma viral oncogene homolog B1 (BRAF) gene. The underlined bases show the position of the common oncogenic T to A mutation V600E (MUTB sequence) compared with the normal sequence (NORB). The outer sequences match the oligonucleotide primers used. As shown in FIG. 5, the forward initiator primer BRF2 contains an abasic site 7 bases from its 3' end. The 3' end of the facilitator oligonucleotide BFol3 contains 6 mismatches to the target DNA and is terminated by a dideoxy GTP to prevent its extension. The facilitator oligonucleotide contains a 19 base region adjacent to the BRF2 primer that matches exactly with the mutant sequence, but contains a single base mismatch to the normal BRAF sequence (gap in underlining). The facilitator oligonucleotide also contains inosines in place of some guanines (see FIG. 5) in the region equivalent to the initiator primer to reduce the stability of the facilitator oligonucleotide/extended reverse strand duplex.

Replicate HDCR amplifications were carried out using a Bio-Rad I Cycler Real-time PCR machine. The forward initiator primer BRF2 was included at 200 nM, the facilitator oligonucleotide BFol3 at 20 nM, and the reverse primer CommR3G at 40 nM; $MgCl_2$ was used at a concentration of 2 mM. The thermocycling conditions were as follows: 95° C. for 2 minutes followed by 60 cycles of 95° C. for 5 seconds, 68° C. or 72° C. for 15 seconds, 83° C. for 10 seconds and 68° C. or 72° C. for 15 seconds. SYBR Green fluorescence was measured at the final step in each cycle.

As observed in FIG. 6, when the annealing/extension thermocycling steps were carried out at 68° C., the amount of amplification product of the mutant sequence was only fractionally larger relative to the normal sequence amplification product. Where as, when the annealing/extension thermocycling steps were carried out at 72° C. the quantity of amplification product of the matched normal template was severely reduced when compared to the mutant template amplification product. The significant temperature dependence of the selective hybridisation of the facilitator oligonucleotide to the mutant sequence compared with the normal (mismatched) sequence can be shown by the major difference seen at the selective temperature (FIG. 6).

Example 3

Selective Amplification and Improved Amplification Efficiency Using HDCR Methodology This example demonstrates both the potential to use HDCR amplification for selective amplification of differentially methylated DNA after bisulphite treatment as well as the advantage of an intermediate heating step in the temperature cycling to improve the efficiency of the two step synthesis of the reverse strand. FIG. 7 shows different nucleic acid sequence templates which were prepared with central regions (underlined) that mimic sequences produced from bisulphite treatment of a region of the hMLH1 gene after bisulphite treatment. Both sequences are flanked by the same sequence for oligonucleotide primer binding. Template M mimics methylated DNA in which cytosines of CpG dinucleotides remain as C after bisulphite treatment. Template U mimics unmethylated DNA where all cytosines are converted to uracil (and subsequently T after amplification). Nucleic acid template was prepared by PCR and diluted 1:100 for addition to HDCR reaction amplifications. Sequences of the initiator primer, facilitator oligonucleotide and reverse primer CommR2G are shown in FIG. 8.

The initiator primer MLH2O has four 2' O-Methyl nucleotides (lower case u) to prevent it giving exponential amplification in absence of facilitator oligonucleotide. The facilitator oligonucleotide MLHF1 has an internal d-spacer (abasic site) that helps prevent background amplification arising from mispriming on the facilitator oligonucleotide. There are also 2 d-spacers close to the 3' end which in combination with a 3' mismatch are expected to interfere with extension of the facilitator oligonucleotide. The remainder of the facilitator oligonucleotide corresponds exactly to the methylated nucleic acid sequence, but also has 3 mismatches with the equivalent unmethylated nucleic acid sequence (FIG. 8).

Replicate HDCR amplifications were carried out in a Corbett Rotor-Gene 3000 Real-time PCR machine. HDCR reaction mixtures contained 200 nM FD oligonucleotide primer MLH2O, 20 nM facilitator oligonucleotide MLHF1 and 40 nM reverse oligonucleotide primer CommR2G. The thermocycling conditions were as follows: 95° C. for 2 minutes followed by 60 cycles of 95° C. for 5 seconds and 65° C. for 40 seconds (FIG. 9A) or 95° C. for 5 seconds, 65° C. for 20 seconds, 74° C. for 10 seconds and 65° C. for 20 seconds (FIG. 9B). Reactions with and without inclusion of an intermediate heating step were compared. Under both conditions amplification from the M template was strongly preferential compared with the U template, but reaction kinetics were much improved with the inclusion of the intermediate heating step, whereby amplification from the M template was advanced by 5 to 10 cycles (FIG. 9B). Even an extra 74° C. step for 10 seconds increases the efficiency of HDCR as would be predicted from the expected mechanism. This step removes the facilitator oligonucleotide from the hybridized and extended target DNA, thus allowing hybridization of the initiator primer once the temperature has been sufficiently reduced.

Example 4

HDCR for Incorporation of Common Outer Priming Sites

This example demonstrates how HDCR can be used to set up an effective multiplexing system. Although the selective amplifications were carried out in separate tubes, the same 'outer' primers were used for both reactions. The two CpG islands chosen for this study are of interest in cancer research because they become hypermethylated in a number of cancers such as colorectal cancer, but remain unmethylated in DNA from normal tissues including blood. FIG. 10 shows the target sequence regions within the TMEFF2 and hMLHI CpG islands (hg18 chr2:192,767,556-192,767,775 (- strand) and hg18 chr3:37,010,130-37,010,262 respectively) and the arrangement of primers and facilitator oligonucleotides relative to the sequence derived from bisulphite-treated methylated DNA.

Template DNAs U and M respectively were either normal blood DNA or blood DNA that had been treated with SssI methylase which is known to convert cytosines in the context of CpG to 5-methyl cytosine (5mC). 5mC is resistant to conversion by bisulphite, whereas unmethylated C is expected to be converted to U (and later to T in amplifications containing dTTP). After bisulphite treatment, all the C's within the tested region that are unmethylated are expected to be converted to U's by bisulphite and later to T's by PCR. Although this bisulphite-converted DNA is referred to as 'U' it should be pointed out that before the experiment was conducted the exact methylation status of the chosen regions in this particular blood DNA sample was not known.

Shown is the selective amplification of the methylated version of a region of the hMLH1 CpG island (within hg18 chr3:37,010,130-37,010,262) and the methylated version of a region of the TMEFF2 CpG island (within hg18 chr2:192,767,556-192,767,775) after bisulphite conversion, using HDCR and 'outer' dependent primers.

The key to this variant of HDCR is the use of initiator primers (FIG. 10). These primers are designed to be able to hybridize to a target sequence and to be extended across the region of interest. However they contain a modification, here a d-spacer, that will prevent them being fully copied. This leads to premature termination of targets opposite or in the vicinity of the modification in the initiator primer and thus a typical polymerase chain reaction is not possible. The facilitator oligonucleotides in this case have 5' tails that do not match those of the initiator primers, but instead match the 5' regions of other dependent primers that are present in the reaction. The facilitator oligonucleotides have a 3' hybridizing part that recognizes regions 3' to the priming region of the initiator primers. A prematurely-terminated target molecule with a sequence that allows hybridization to the facilitator oligonucleotide can copy the 5' tails of the facilitator oligonucleotides. This generates a primer binding sites for an 'outer' facilitator oligonucleotide dependent primer. Because these dependent primers also contain modifications (d-spacers) that prevent full copying, amplification depends on the continued regeneration of the binding sites for the dependent primers by copying of the facilitator oligonucleotides during every cycle. In the example given here, the initiator primers were designed to be able to prime on both M and U variants of their targets. In other words, priming is designed to be specific to the bisulphite-converted sequence, but not give any specificity to either the M or U variants. To do this, CpG sequences in which the variations in methylation are present are avoided as far as possible. Where CpG positions do lie within the binding sites of the Initiators, a mix of C and T (or G and A, depending on the strand targeted) are used within the initiator so that it can bind to both M and U. The only specificity for the M sequence variant is within the hybridizing regions of the facilitator oligonucleotides, which match the M sequence but not the U sequence.

The oligonucleotide sequences (5' to 3') and their concentrations used in HDCR for the TMEFF2 target were:

```
250 nM TMEFInL1
                                            (SEQ ID NO: 17)
TTTTTAGAGTTTTTTTTTTATGGTAGTAGTTTTT
250 nM TMEFInR1
                                            (SEQ ID NO: 21)
CCRAACAACRAACTACTAAACATCCC
40 nM TMEFLdS170
                                            (SEQ ID NO: 18)
TGGCCCGTCGCCGTCCCTCTGTTTTGCTGTATTTCGCGTTTTCGGCAA
ddG
40 nM TMEFRdS133
                                            (SEQ ID NO: 22)
CACACGTCGCTCGGGCCTGTGTTCTTGTCAACCCGCGAACGACGGA ddG
500 nM MCD6
                                            (SEQ ID NO: 19)
TGG555GT5G55GT555T5TGATTTGCT
500 nM MCD4
                                            (SEQ ID NO: 23)
CA5A5GT5G5T5GGG55TGTGATCTTGT
```

-continued 100 nM TPEFMC
(SEQ ID NO: 32)
HEX-AAATTTTCGAGATTATGCGCGGGT TAMRA

And for the hMLH1 target:

250 nM MLHInit2
(SEQ ID NO: 26)
AATGTTATTAAAGAGATGATTGAGAΔTTGGTA 250 nM MLHInit1
(SEQ ID NO: 29)
CTATACATACCTCTACCCRAACAΔAAAAAC 40 nM 131hMLHFoldS2
(SEQ ID NO: 30)
CACACGTCGCTCGGGCCTGTGTTCTTGTAAAAΔCGTATCCGCGCCAGG-ddG 40 nM RMLH170
(SEQ ID NO: 27)
TGGCCCGTCGCCGTCCCICTGTTTTGCTTTGΔTACGGAGGGAGTCGCC-ddG 500 nM MCD6
(SEQ ID NO: 19)
TGG555GT5G55GT555T5TGΔTTTGCT 500 nM MCD4
(SEQ ID NO: 23)
CA5A5GT5G5T5GGG55TGTGΔTCTTGT 100 nM hMLH
(SEQ ID NO: 33)
HEX-ACGCGACCCGTTAAATCGTAACCCT BHQ1

Where Δ=d-spacer, 5=methyl cytosine, ddG=dideoxy guanosine introduced using Terminal Transferase, R=mixture of A and G, HEX=hexachloro-6-carboxyfluorescein, TAMRA=6-carboxytetramethylrhodamine, BHQ1=Black Hole Quencher 1. Underlined bases=mismatches that in conjunction with the added ddG reduce or eliminate extension.

HDCR's in duplicate were carried out in 10 microlitre volumes containing 1× Platinum Taq buffer [20 mM Tris-HCl (pH 8.4) and 50 mM KCl], 4 mM MgCl₂, 0.2 mM dATP, 0.2 mM dCTP, 0.2 mM dGTP, 0.4 mM dUTP, 1/25,000 dilution of SYBR Green, 10 nM fluorescein and 0.4 units of Platinum Taq DNA polymerase (hot start) from Invitrogen. 1 nanogram of human blood DNA that had been methylated in vitro using SssI methylase and then bisulphite-treated (M) was compared to the same blood DNA that was also bisulphite-treated but had not undergone the SssI methylase treatment (U). The cycling was carried out using a RotorGene 3000 (72 tube rotor) with the program: 90 C 5 s, 95 C 2 m then 10 cycles of 90 C 5 s, 95 C 15 s, 50 C 2 m, 80 C 10 s, 60 C 2 m then a single incubation at 60 C for 15 s with a read on the FAM/SYBR channel (so that auto-calibration would be done at this temperature) then 60 cycles of 90 C 15 s, 50 C 1 m, 80 C 10 s, 60 C 1 m with reading at 90 C in the JOE channel (to detect hydrolysis of the HEX TaqMan probes) and at 60 C in the FAM/SYBR channel (to detect production of double stranded DNA). The 90 C 5 s steps were included to prevent any overshoot of temperature when ramping to the next step, 95 C. In earlier experiments it had been found that ramping directly to 95 C from a much lower temperature can be deleterious when using volumes such as 10 microlitres in the RotorGene 3000.

The successful amplification of methylated sequences for two different targets, TMEFF2 (panel A) and hMLH1 (panel B) is shown in FIG. 11. The production of HEX fluorescence due to the hydrolysis of a hydrolysis probe indicates the successful amplification of the methylated version. This occurs for both TMEFF2 and hMLH1 targets. The presence of SYBR Green allows detection of any other amplified DNA. It can be seen that non-target sequences are amplified very poorly in the case of TMEFF2, and not amplified at all in the case of hMLH1. A d-spacer has been included within the hybridizing region of each facilitator oligonucleotide in this example. One advantage of this is that this lowers the melting temperature of the facilitator oligonucleotide thus reducing its ability to compete with the facilitator oligonucleotide-dependent primer for binding to repaired target. A second possible advantage is to prevent copying of the 5' region of the facilitator oligonucleotide by extension from non-target molecules that have chance partial or complete matches to regions of the facilitator oligonucleotide's hybridizing region 3' to the d-spacer. The same dependent primers were used in both cases, thus indicating the possibility of achieving a multiplexed HDCR system in which specificity for particular target(s) is achieved through use of initiators and facilitator oligonucleotides, with a single pair of dependent primers able to amplify any or all of the targets that are present.

Example 5

Oligonucleotide Dependency of HDCR

This example which uses the hMLH1 target shows that all three oligonucleotides (considering just one end of the target) are needed for the HDCR. The buffer and cycling conditions were the same as used in the previous example for hMLH1, but in this case all reactions contained 1 nanogram of bisulphite-converted SssI-methylated DNA (M). Some of the duplicate reactions lacked a particular oligonucleotide in order to establish the requirement for that oligonucleotide for a successful HDCR. Both HEX (hydrolysis probe) and SYBR Green were read at the 60° C. step during the stage that contains fifty cycles. The results are shown in FIG. 12. There was little difference between the curves obtained using the hydrolysis probe and SYBR Green, suggesting that the hMLH1 target was specifically amplified. When all three of the tested oligonucleotides were present, amplification was first detected shortly after cycle 20. When MLHInit2, which is one of the initiators, was omitted from the reaction, amplification could only be detected after cycle 35 for one of the reactions. In the other duplicate reaction, amplification was not detected. Omission of either the facilitator oligonucleotide RMLH170, or the outer dependent primer MCD6 resulted in very late amplification. This shows that a successful HDCR depends upon the inclusion of all three oligonucleotides. The corresponding oligonucleotides directed at the other end of the target were present in all of the reactions.

The invention claimed is:

1. A method for the selective amplification of a target nucleotide sequence located within a nucleic acid molecule, the method comprising:

(a) denaturing a nucleic acid molecule ("template" nucleic acid molecule) comprising a target nucleotide sequence to produce a denatured template nucleic acid molecule and contacting the denatured template nucleic acid molecule with at least one initiator primer, wherein the initiator primer is modified such that the presence of the modification prematurely terminates complementary strand synthesis;

(b) initiating second strand synthesis from the initiator primer to produce a double-stranded nucleic acid molecule, wherein the modification of the initiator primer is introduced into the newly synthesized second strand;

(c) denaturing the double-stranded molecule produced in (b) and contacting the resulting denatured double-stranded molecule with a primer that binds to the opposite end of the target nucleotide sequence to that which the initiator primer binds;

(d) initiating reverse strand synthesis from the primer to produce a double-stranded nucleic acid molecule; whereby reverse strand synthesis prematurely terminates due to the modification introduced in (b) to produce an incomplete reverse strand;

(e) denaturing the double-stranded molecule synthesized in (d) and contacting the resulting denatured double-stranded molecule with a facilitator oligonucleotide that binds to the incomplete reverse strand,
wherein the facilitator oligonucleotide:
includes at least one modification at or near its 3' terminus such that 3' extension from the facilitator oligonucleotide is blocked;
binds to substantially the same or an adjacent region of the template nucleic acid molecule as the initiator primer; and
comprises sequences complementary to the target sequence 3' to the binding location of the initiator primer;

(f) initiating strand extension from the facilitator oligonucleotide to complete the reverse strand; and (g) optionally repeating steps (a) to (f) for one or more additional cycles.

2. The method of claim 1 wherein the 5' region of the facilitator oligonucleotide shares:

(i) sufficient sequence identity with the initiator primer such that the initiator primer binding site is regenerated following strand extension initiated from the facilitator oligonucleotide thereby enabling the initiator primer to initiate further rounds of strand synthesis, or (ii) insufficient sequence identity with the initiator primer such that the initiator primer binding site is not regenerated following strand synthesis initiated from the facilitator oligonucleotide.

3. The method of claim 2 wherein where there is (ii) insufficient sequence identity between the 5' region of the facilitator oligonucleotide and the initiator primer, the method further employs a facilitator oligonucleotide-dependent primer, modified such that the presence of the modification prematurely terminates complementary strand synthesis, which primer shares sufficient sequence identity with the 5' region of the facilitator oligonucleotide such that strand synthesis initiated from the facilitator oligonucleotide generates a facilitator oligonucleotide-dependent primer binding site thereby enabling the facilitator oligonucleotide-dependent primer to initiate further rounds of strand synthesis.

4. The method of claim 3 wherein the 5' terminus of the facilitator oligonucleotide coincides with the 5' terminus of or falls within the facilitator oligonucleotide-dependent primer.

5. The method of claim 3 wherein the facilitator oligonucleotide comprises an extended 5' tail comprising sequence additional to that present at the 5' end of the facilitator oligonucleotide-dependent primer.

6. The method of claim 3 wherein the facilitator oligonucleotide-dependent primer is modified by the inclusion of one or more spacers, abasic sites or modified nucleotides.

7. The method of claim 6 wherein the modification in the facilitator oligonucleotide-dependent primer is located sufficiently near to the 3' terminus of the primer such that whilst the primer retains the ability to initiate 3' extension, when the extended product containing the modification within its primer sequence is copied, the complementary strand is prematurely truncated preventing primer binding in subsequent amplification cycles.

8. The method of claim 6, wherein the modified nucleotide is a 2'-O-methyl nucleotide.

9. The method of claim 1 wherein the at least one modification that blocks 3' extension of the facilitator oligonucleotide includes the incorporation of one or more non-extendible moieties or nucleotide analogues at or near the 3' terminus.

10. The method of claim 9 wherein the at least one modification comprises a single 3' terminal non-extendible base or base analogue, a combination of a 3' terminal non-extendible base and one or more nucleotide mismatches near the 3' terminus of the oligonucleotide, and/or the incorporation of abasic sites near the 3' terminus of the oligonucleotide.

11. The method of claim 10 wherein the non-extendible base is selected from a 2',3' dideoxynucleotide, a 3' C3, C18 or other length spacer, a 3' phosphorylated nucleotide, a "peptide nucleic acid" base, a "locked nucleic acid" (LNA) base, a nucleotide amine derivative, uracil treated with Uracil DNA glycosylase, RNA or a 2' O-methyl nucleotide, or a combination of these.

12. The method of claim 1 wherein the initiator primer is modified by the inclusion of one or more spacers, abasic sites or modified nucleotides.

13. The method of claim 12 wherein the modification in the initiator primer is located sufficiently near to the 3' terminus of the primer such that whilst the primer retains the ability to initiate 3' extension, when the extended product containing the modification within its primer sequence is copied, the complementary strand is prematurely truncated preventing primer binding in subsequent amplification cycles.

14. The method of claim 12, wherein the modified nucleotide is a 2'-O-methyl nucleotide.

15. The method of claim 1 wherein the 5' terminus of the facilitator oligonucleotide coincides with the 5' terminus of or falls within the initiator primer.

16. The method of claim 1 wherein the facilitator oligonucleotide comprises an extended 5' tail comprising sequence additional to that present at the 5' end of the initiator primer.

17. The method of claim 1 wherein both oligonucleotide primers flanking the target sequence are initiator primers and the method employs two facilitator oligonucleotides, one of which binds to substantially the same or adjacent regions of the template nucleic acid molecule as the forward initiator primer and the other binds to substantially the same or adjacent regions of the template nucleic acid molecule as the reverse initiator primer.

18. The method of claim 17 wherein the 5' region of at least one facilitator oligonucleotide shares:
(i) sufficient sequence identity with the corresponding initiator primer such that the initiator primer binding site is regenerated following strand extension initiated from the at least one facilitator oligonucleotide thereby enabling the corresponding initiator primer to initiate further rounds of strand synthesis, or
(ii) insufficient sequence identity with the corresponding initiator primer such that the initiator primer binding site is not regenerated following strand synthesis initiated from the at least one facilitator oligonucleotide.

19. The method of claim 18 wherein where there is (ii) insufficient sequence identity between the 5' region of the facilitator oligonucleotide and the initiator primer, the method further employs at least one facilitator oligonucleotide-dependent primer, modified such that the presence of the modification prematurely terminates complementary strand synthesis, which primer shares sufficient sequence identity with the 5' region of the corresponding facilitator oligonucleotide such that strand synthesis initiated from the facilitator oligonucleotide generates a facilitator oligonucleotide-dependent primer binding site thereby enabling the facilitator oligonucleotide-dependent primer to initiate further rounds of strand synthesis.

20. The method of claim 19 wherein the method employs two facilitator oligonucleotide-dependent primers, one of which binds to substantially the same or adjacent regions of the template nucleic acid molecule as one facilitator oligonucleotide and the other binds to substantially the same or adjacent regions of the template nucleic acid molecule as the other facilitator oligonucleotide.

21. The method of claim 1 wherein the method is employed in DNA methylation analysis and/or in the diagnosis of, or predictor of susceptibility to, a disease or condition in a subject, which disease or condition is characterized by or associated with an alteration in a genetic sequence.

22. A method for detecting a variant nucleotide sequence by selectively amplifying a target nucleotide sequence located within a nucleic acid molecule and comprising the variant sequence, wherein the method comprises:
(a) denaturing a nucleic acid molecule ("template nucleic acid molecule") comprising a target nucleotide sequence comprising a variant sequence to produce a denatured template molecule and contacting the denatured template nucleic acid molecule with at least one initiator primer, wherein the initiator primer is modified such that the presence of the modification prematurely terminates complementary strand synthesis;
(b) initiating second strand synthesis from the initiator primer to produce a double-stranded nucleic acid molecule, wherein the modification from the initiator primer is introduced into the newly synthesized second strand;
(c) denaturing the double-stranded molecule produced in (b) and contacting the resulting denatured double-stranded molecule with a primer that binds to the opposite end of the target nucleotide sequence to that which the initiator primer binds;
(d) initiating reverse strand synthesis from the primer to produce a double-stranded nucleic acid molecule, whereby reverse strand synthesis prematurely terminates due to the modification introduced in (b) to produce an incomplete reverse strand;
(e) denaturing the double-stranded molecule synthesized in (d) and contacting the resulting denatured double-stranded molecule with a facilitator oligonucleotide that binds to the incomplete reverse strand, wherein the facilitator oligonucleotide:
includes at least one modification at or near its 3' terminus such that 3' extension from the facilitator oligonucleotide is blocked;
binds to substantially the same or an adjacent region of the template nucleic acid molecule as the initiator primer; and
comprises sequences complementary to the target sequence 3' to the binding location of the initiator primer; wherein said 3' sequences enable preferential binding of the facilitator oligonucleotide to the target nucleotide sequence comprising the variant nucleotide sequence rather than to a corresponding nonvariant nucleotide sequence;
(f) initiating strand extension from the facilitator oligonucleotide to complete the reverse strand;

(g) optionally repeating steps (a) to (f) for one or more additional cycles; and comparing the nucleotide sequence of the amplified product with a corresponding sequence comprising the non-variant nucleotide sequence, to detect the variant nucleotide sequence.

23. The method of claim 22 wherein the variant sequence comprises the addition, deletion or substitution of one or more nucleotides or a modification, such as altered methylation status, to one or more nucleotides within the target sequence.

24. The method of claim 23, wherein the modification is an altered methylation status.

* * * * *

UNITED STATES PATENT AND TRADEMARK OFFICE
CERTIFICATE OF CORRECTION

PATENT NO. : 8,455,197 B2  Page 1 of 1
APPLICATION NO. : 12/681603
DATED : June 4, 2013
INVENTOR(S) : Keith Norman Rand It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 293 days.

Signed and Sealed this
Eighth Day of September, 2015

Michelle K. Lee
*Director of the United States Patent and Trademark Office*